US012708469B2

(12) United States Patent
Sadaka

(10) Patent No.: US 12,708,469 B2
(45) Date of Patent: Aug. 18, 2026

(54) LOW-FRICTION MEDICAL TOOLS HAVING ROLLER-ASSISTED TENSION MEMBERS

(71) Applicant: Intuitive Surgical Operations, Inc., Sunnyvale, CA (US)

(72) Inventor: Alain Sadaka, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 19/201,089

(22) Filed: May 7, 2025

(65) Prior Publication Data

US 2025/0325338 A1 Oct. 23, 2025

Related U.S. Application Data

(63) Continuation of application No. 18/640,575, filed on Apr. 19, 2024, now Pat. No. 12,303,226, which is a (Continued)

(51) Int. Cl.
*A61B 34/00* (2016.01)
*A61B 17/28* (2006.01)
(Continued)

(52) U.S. Cl.
CPC ............ *A61B 34/71* (2016.02); *B25J 15/022* (2013.01); *A61B 17/29* (2013.01); (Continued)

(58) Field of Classification Search
CPC ............ A61B 17/29; A61B 17/320016; A61B 2018/00595; A61B 34/35; A61B 34/71; A61B 2023/715; B25J 15/022
See application file for complete search history.

(56) References Cited

U.S. PATENT DOCUMENTS 4,341,144 A 7/1982 Milne
5,325,845 A 7/1994 Adair
(Continued)

FOREIGN PATENT DOCUMENTS

CA 2853431 A1 5/2013
CN 102458551 A 5/2012
(Continued)

OTHER PUBLICATIONS

Extended European Search Report for Application No. EP19763829.9, mailed on Oct. 25, 2021, 9 pages.
(Continued)

*Primary Examiner* — Adam D Rogers

(57) ABSTRACT

A low-friction medical device is provided having roller-assisted tension members and a friction-reducing curved guide path. The device includes a first link, a second link, and a tension member. A proximal end portion of the first link is coupled to an instrument shaft. A proximal end portion of the second link is rotatably coupled to a distal end portion of first link about a first axis. The second link defines a curved guide path and a cable extends from the first link through the curved guide path to a distal end of the second link and couples with a tool member. A roller having a roller surface is coupled to the second link such that the roller surface is aligned with a portion of the curved path and contacts the cable therein. The curved guide surface has a small fleet angle.

18 Claims, 23 Drawing Sheets

Related U.S. Application Data continuation of application No. 16/971,974, filed as application No. PCT/US2019/020651 on Mar. 5, 2019, now Pat. No. 11,992,286.

(60) Provisional application No. 62/639,628, filed on Mar. 7, 2018.

(51) Int. Cl.

| | |
|---|---|
| ***A61B 17/32*** | (2006.01) |
| ***A61B 18/00*** | (2006.01) |
| ***A61B 34/35*** | (2016.01) |
| ***B25J 15/02*** | (2006.01) |
| *A61B 17/29* | (2006.01) |

(52) U.S. Cl.

CPC ................. *A61B 17/320016* (2013.01); *A61B 2018/00595* (2013.01); *A61B 34/35* (2016.02); *A61B 2034/715* (2016.02)

(56) References Cited

U.S. PATENT DOCUMENTS

| | | | |
|---|---|---|---|
| 5,396,900 | A | 3/1995 | Slater et al. |
| 5,482,054 | A | 1/1996 | Slater et al. |
| 5,624,398 | A | 4/1997 | Smith et al. |
| 5,784,542 | A | 7/1998 | Ohm et al. |
| 5,792,135 | A | 8/1998 | Madhani et al. |
| 5,807,377 | A | 9/1998 | Madhani et al. |
| 5,855,583 | A | 1/1999 | Wang et al. |
| 5,876,325 | A | 3/1999 | Mizuno et al. |
| 5,899,914 | A | 5/1999 | Zirps et al. |
| 5,916,146 | A | 6/1999 | Allotta et al. |
| 6,007,550 | A | 12/1999 | Wang et al. |
| 6,197,017 | B1 | 3/2001 | Brock et al. |
| 6,206,903 | B1 | 3/2001 | Ramans |
| 6,309,397 | B1 | 10/2001 | Julian et al. |
| 6,331,181 | B1 | 12/2001 | Tierney et al. |
| 6,371,952 | B1 | 4/2002 | Madhani et al. |
| 6,394,998 | B1 | 5/2002 | Wallace et al. |
| 6,491,626 | B1 | 12/2002 | Stone et al. |
| 6,491,701 | B2 | 12/2002 | Tierney et al. |
| 6,554,844 | B2 | 4/2003 | Lee et al. |
| 6,676,684 | B1 | 1/2004 | Morley et al. |
| 6,685,698 | B2 | 2/2004 | Morley et al. |
| 6,767,349 | B2 | 7/2004 | Ouchi |
| 6,817,974 | B2 | 11/2004 | Cooper et al. |
| 6,843,793 | B2 | 1/2005 | Brock et al. |
| 6,949,106 | B2 | 9/2005 | Brock et al. |
| 6,969,385 | B2 | 11/2005 | Moreyra |
| 6,994,708 | B2 | 2/2006 | Manzo |
| 7,083,571 | B2 | 8/2006 | Wang et al. |
| 7,090,683 | B2 | 8/2006 | Brock et al. |
| 7,125,403 | B2 | 10/2006 | Julian et al. |
| 7,147,650 | B2 | 12/2006 | Lee |
| 7,169,141 | B2 | 1/2007 | Brock et al. |
| 7,214,230 | B2 | 5/2007 | Brock et al. |
| 7,316,681 | B2 | 1/2008 | Madhani et al. |
| 7,320,700 | B2 | 1/2008 | Cooper et al. |
| 7,338,505 | B2 | 3/2008 | Belson |
| 7,338,513 | B2 | 3/2008 | Lee et al. |
| 7,371,210 | B2 | 5/2008 | Brock et al. |
| 7,608,083 | B2 | 10/2009 | Lee et al. |
| 7,682,307 | B2 | 3/2010 | Danitz et al. |
| 7,699,835 | B2 | 4/2010 | Lee et al. |
| 7,785,252 | B2 | 8/2010 | Danitz et al. |
| 7,824,401 | B2 | 11/2010 | Manzo et al. |
| 7,935,130 | B2 | 5/2011 | Williams |
| 8,142,421 | B2 | 3/2012 | Cooper et al. |
| 8,142,447 | B2 | 3/2012 | Cooper et al. |
| 8,245,595 | B2 | 8/2012 | Milenkovic |
| 8,347,757 | B2 | 1/2013 | Duval |
| 8,398,634 | B2 * | 3/2013 | Manzo .................. A61B 18/14 606/41 |
| 8,479,969 | B2 | 7/2013 | Shelton, IV |
| 8,540,748 | B2 | 9/2013 | Murphy et al. |
| 8,551,115 | B2 | 10/2013 | Steger et al. |
| 8,578,810 | B2 | 11/2013 | Donhowe |
| 8,602,288 | B2 | 12/2013 | Shelton, IV et al. |
| 8,771,270 | B2 | 7/2014 | Burbank |
| 8,800,838 | B2 | 8/2014 | Shelton, IV |
| 8,821,480 | B2 | 9/2014 | Burbank |
| 8,939,963 | B2 | 1/2015 | Rogers et al. |
| 9,028,494 | B2 | 5/2015 | Shelton, IV et al. |
| 9,055,961 | B2 | 6/2015 | Manzo et al. |
| 9,078,684 | B2 | 7/2015 | Williams |
| 9,198,729 | B2 | 12/2015 | Rogers |
| 9,204,923 | B2 | 12/2015 | Manzo et al. |
| 9,232,979 | B2 | 1/2016 | Parihar et al. |
| 9,259,275 | B2 | 2/2016 | Burbank |
| 9,358,031 | B2 | 6/2016 | Manzo |
| 9,533,122 | B2 | 1/2017 | Weitzner et al. |
| 9,615,846 | B2 | 4/2017 | Prestel |
| 9,962,228 | B2 | 5/2018 | Schuh et al. |
| 10,130,366 | B2 | 11/2018 | Shelton, IV et al. |
| 10,285,763 | B2 | 5/2019 | Vale et al. |
| 10,299,873 | B2 | 5/2019 | Hares et al. |
| 10,499,891 | B2 | 12/2019 | Chaplin et al. |
| 10,524,870 | B2 | 1/2020 | Saraliev et al. |
| 10,624,703 | B2 | 4/2020 | Chaplin et al. |
| 10,682,141 | B2 | 6/2020 | Moore et al. |
| 10,758,298 | B2 | 9/2020 | Felder et al. |
| 10,786,320 | B2 | 9/2020 | Adams et al. |
| 10,792,116 | B2 | 10/2020 | Haraguchi et al. |
| 10,813,706 | B2 | 10/2020 | Chaplin et al. |
| 11,020,112 | B2 | 6/2021 | Shelton, IV et al. |
| 11,045,270 | B2 | 6/2021 | Shelton, IV et al. |
| 11,109,928 | B2 | 9/2021 | Schuh |
| 11,129,686 | B2 | 9/2021 | Chaplin et al. |
| 11,241,290 | B2 | 2/2022 | Waterbury et al. |
| 11,259,798 | B2 | 3/2022 | Limon et al. |
| 11,272,977 | B2 | 3/2022 | Manzo et al. |
| 11,291,514 | B2 | 4/2022 | Shuh et al. |
| 11,357,566 | B2 | 6/2022 | Manzo et al. |
| 11,439,376 | B2 | 9/2022 | Ratia et al. |
| 11,452,572 | B2 | 9/2022 | Abbott et al. |
| 11,612,447 | B2 | 3/2023 | Limon et al. |
| 11,666,374 | B2 | 6/2023 | Burbank et al. |
| 11,717,364 | B2 | 8/2023 | Penny et al. |
| 11,992,286 | B2 | 5/2024 | Sadaka |
| 11,992,287 | B2 | 5/2024 | Duque et al. |
| 12,082,900 | B2 | 9/2024 | Ratia et al. |
| 12,257,014 | B2 * | 3/2025 | Comenencia Ortiz ... G01L 1/22 |
| 12,303,226 | B2 * | 5/2025 | Sadaka .................. A61B 34/71 |
| 2001/0025134 | A1 | 9/2001 | Bon et al. |
| 2002/0111621 | A1 | 8/2002 | Wallace et al. |
| 2004/0260198 | A1 | 12/2004 | Rothberg et al. |
| 2004/0266574 | A1 | 12/2004 | Jinno et al. |
| 2005/0240178 | A1 | 10/2005 | Morley et al. |
| 2006/0074415 | A1 | 4/2006 | Scott et al. |
| 2006/0131908 | A1 | 6/2006 | Tadano |
| 2006/0190034 | A1 | 8/2006 | Nishizawa et al. |
| 2007/0158385 | A1 | 7/2007 | Hueil et al. |
| 2007/0208375 | A1 | 9/2007 | Nishizawa et al. |
| 2007/0246508 | A1 | 10/2007 | Green |
| 2008/0046122 | A1 | 2/2008 | Manzo et al. |
| 2008/0065102 | A1 | 3/2008 | Cooper |
| 2008/0065105 | A1 | 3/2008 | Larkin et al. |
| 2008/0125794 | A1 | 5/2008 | Brock et al. |
| 2008/0196533 | A1 | 8/2008 | Bergamasco et al. |
| 2008/0255421 | A1 | 10/2008 | Hegeman et al. |
| 2009/0088774 | A1 | 4/2009 | Swarup et al. |
| 2009/0171348 | A1 | 7/2009 | Guo et al. |
| 2009/0198272 | A1 | 8/2009 | Kerver et al. |
| 2009/0326530 | A1 | 12/2009 | Orban, III et al. |
| 2010/0030238 | A1 | 2/2010 | Viola et al. |
| 2010/0198218 | A1 | 8/2010 | Manzo |
| 2010/0198253 | A1 | 8/2010 | Jinno et al. |
| 2011/0295269 | A1 | 12/2011 | Swensgard et al. |
| 2011/0295270 | A1 | 12/2011 | Giordano et al. |
| 2012/0330287 | A1 | 12/2012 | Yim |
| 2013/0123783 | A1 | 5/2013 | Marczyk et al. |
| 2013/0144395 | A1 | 6/2013 | Stefanchik et al. |
| 2013/0158542 | A1 | 6/2013 | Manzo et al. |

(56) References Cited

U.S. PATENT DOCUMENTS

| | | | |
|---|---|---|---|
| 2013/0239735 | A1 | 9/2013 | Solomon et al. |
| 2013/0304084 | A1 | 11/2013 | Beira et al. |
| 2013/0345718 | A1 | 12/2013 | Crawford et al. |
| 2014/0005662 | A1 | 1/2014 | Shelton, IV |
| 2014/0005678 | A1 | 1/2014 | Shelton, IV et al. |
| 2014/0005708 | A1 | 1/2014 | Shelton, IV |
| 2014/0073856 | A1 | 3/2014 | Stein et al. |
| 2014/0100558 | A1 | 4/2014 | Schmitz et al. |
| 2014/0114327 | A1 | 4/2014 | Boudreaux et al. |
| 2014/0257331 | A1 | 9/2014 | Kim et al. |
| 2014/0276956 | A1 | 9/2014 | Crainich et al. |
| 2015/0005786 | A1 | 1/2015 | Burbank |
| 2015/0150635 | A1 | 6/2015 | Kilroy et al. |
| 2015/0157355 | A1 | 6/2015 | Price et al. |
| 2015/0313676 | A1 | 11/2015 | Deodhar |
| 2016/0051274 | A1 | 2/2016 | Howell et al. |
| 2016/0051318 | A1 | 2/2016 | Manzo et al. |
| 2016/0058443 | A1 | 3/2016 | Yates et al. |
| 2016/0143688 | A1 | 5/2016 | Orban, III et al. |
| 2016/0287279 | A1 | 10/2016 | Bovay et al. |
| 2016/0287346 | A1 | 10/2016 | Hyodo et al. |
| 2016/0296219 | A1 | 10/2016 | Srivastava et al. |
| 2016/0302819 | A1 | 10/2016 | Stulen et al. |
| 2016/0303743 | A1 | 10/2016 | Rockrohr |
| 2016/0361123 | A1 | 12/2016 | Hares et al. |
| 2017/0007242 | A1 | 1/2017 | Shelton, IV et al. |
| 2017/0007345 | A1 | 1/2017 | Smith et al. |
| 2017/0042562 | A1 | 2/2017 | Moody et al. |
| 2017/0095922 | A1 | 4/2017 | Licht et al. |
| 2017/0120457 | A1 | 5/2017 | Saraliev et al. |
| 2017/0234411 | A1 | 8/2017 | Dewaele et al. |
| 2017/0252096 | A1 | 9/2017 | Felder et al. |
| 2017/0265954 | A1 | 9/2017 | Burbank et al. |
| 2018/0200895 | A1 | 7/2018 | Kan |
| 2019/0094084 | A1 | 3/2019 | Swinehart et al. |
| 2019/0099227 | A1 | 4/2019 | Rockrohr |
| 2019/0099231 | A1 | 4/2019 | Bruehwiler et al. |
| 2019/0159846 | A1 | 5/2019 | Yates et al. |
| 2019/0167368 | A1 | 6/2019 | Yoshii |
| 2019/0192137 | A1 | 6/2019 | Shelton, IV et al. |
| 2019/0231374 | A1 | 8/2019 | Kimura et al. |
| 2019/0239877 | A1 | 8/2019 | Ragosta et al. |
| 2019/0239967 | A1 | 8/2019 | Ragosta et al. |
| 2019/0336228 | A1 | 11/2019 | Blumenkranz et al. |
| 2019/0380800 | A1 | 12/2019 | Jogasaki et al. |
| 2020/0054405 | A1 | 2/2020 | Schuh et al. |
| 2020/0054408 | A1 | 2/2020 | Schuh et al. |
| 2020/0093554 | A1 | 3/2020 | Schuh et al. |
| 2020/0138531 | A1 | 5/2020 | Chaplin |
| 2020/0170734 | A1 | 6/2020 | Saraliev et al. |
| 2020/0197112 | A1 | 6/2020 | Chin et al. |
| 2020/0352660 | A1 | 11/2020 | Prisco |
| 2020/0383738 | A1 | 12/2020 | Abbott et al. |
| 2020/0383739 | A1 | 12/2020 | Abbott et al. |
| 2021/0244427 | A1 | 8/2021 | Lee et al. |
| 2021/0290322 | A1 | 9/2021 | Traina |
| 2022/0022943 | A1 | 1/2022 | Manzo et al. |
| 2022/0096184 | A1 | 3/2022 | Ergueta et al. |
| 2022/0218329 | A1 | 7/2022 | Limon et al. |
| 2022/0354474 | A1 | 11/2022 | Ratia et al. |
| 2023/0190398 | A1 | 6/2023 | Limon et al. |
| 2023/0293160 | A1 | 9/2023 | Waterbury |
| 2024/0341887 | A1 | 10/2024 | Sadaka |
| 2024/0390090 | A1 | 11/2024 | Ye et al. |

FOREIGN PATENT DOCUMENTS

| | | | |
|---|---|---|---|
| CN | 102488554 | A | 6/2012 |
| CN | 104116547 | A | 10/2014 |
| CN | 106714721 | A | 5/2017 |
| CN | 113262051 | A | 8/2021 |
| EP | 1847289 | A2 | 10/2007 |
| EP | 2362285 | A2 | 8/2011 |
| EP | 2415418 | A1 | 2/2012 |
| EP | 2548529 | A1 | 1/2013 |
| EP | 2783643 | A1 | 10/2014 |
| EP | 3100666 | A1 | 12/2016 |
| EP | 3103374 | A1 | 12/2016 |
| FR | 3016543 | A1 | 7/2015 |
| GB | 191012759 | A | 3/1911 |
| GB | 2590881 | A | 7/2021 |
| JP | 2002503131 | A | 1/2002 |
| JP | 2002200091 | A | 7/2002 |
| JP | 2006061364 | A | 3/2006 |
| KR | 100778387 | B1 | 11/2007 |
| WO | WO-2009123891 | A1 | 10/2009 |
| WO | WO-2010081050 | A1 | 7/2010 |
| WO | WO-2011097095 | A1 | 8/2011 |
| WO | WO-2012006306 | A2 | 1/2012 |
| WO | WO-2013181522 | A1 | 12/2013 |
| WO | WO-2014025204 | A1 | 2/2014 |
| WO | WO-2014151952 | A1 | 9/2014 |
| WO | WO-2015088647 | A1 | 6/2015 |
| WO | WO-2016025132 | A1 | 2/2016 |
| WO | WO-2016161449 | A1 | 10/2016 |
| WO | WO-2016189284 | A1 | 12/2016 |
| WO | WO-2017064301 | A1 | 4/2017 |
| WO | WO-2017064303 | A1 | 4/2017 |
| WO | WO-2017064306 | A1 | 4/2017 |
| WO | WO-2017098273 | A1 | 6/2017 |
| WO | WO-2017136710 | A2 | 8/2017 |
| WO | WO-2017188851 | A1 | 11/2017 |
| WO | WO-2017209695 | A1 | 12/2017 |
| WO | WO-2018049211 | A1 | 3/2018 |
| WO | WO-2018069679 | A1 | 4/2018 |
| WO | WO-2018094191 | A1 | 5/2018 |
| WO | WO-2018123024 | A1 | 7/2018 |
| WO | WO-2018179140 | A1 | 10/2018 |
| WO | WO-2018234795 | A1 | 12/2018 |
| WO | WO-2018234814 | A1 | 12/2018 |
| WO | WO-2019118334 | A1 | 6/2019 |
| WO | WO-2019118336 | A1 | 6/2019 |
| WO | WO-2019118337 | A1 | 6/2019 |
| WO | WO-2019173267 | A1 | 9/2019 |
| WO | WO-2022072732 | A1 | 4/2022 |
| WO | WO-2023022913 | A1 | 2/2023 |
| WO | WO-2023177565 | A1 | 9/2023 |

OTHER PUBLICATIONS

International Search Report and Written Opinion for Application No. PCT/US2019/020651, mailed on Jun. 4, 2019, 7 pages.

Office Action for U.S. Appl. No. 16/971,974, mailed Oct. 6, 2023, 15 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FIG. 2
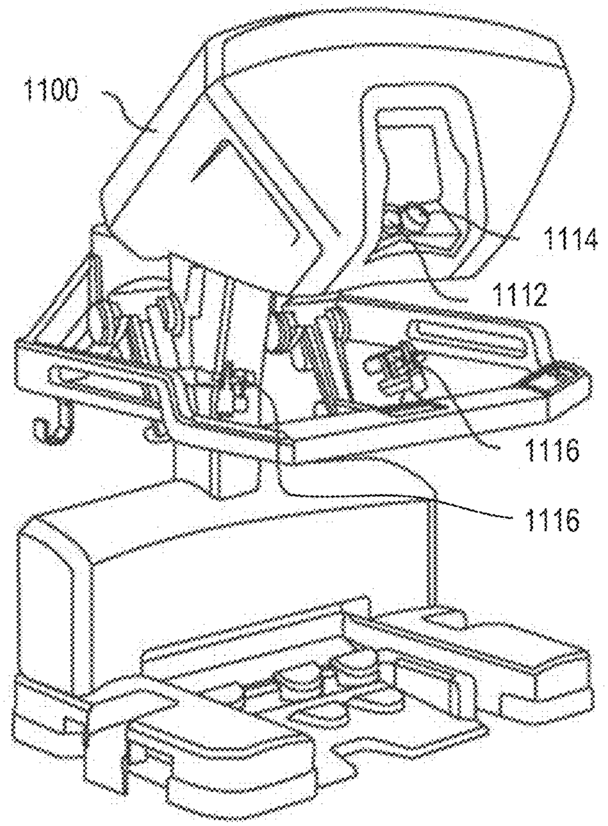
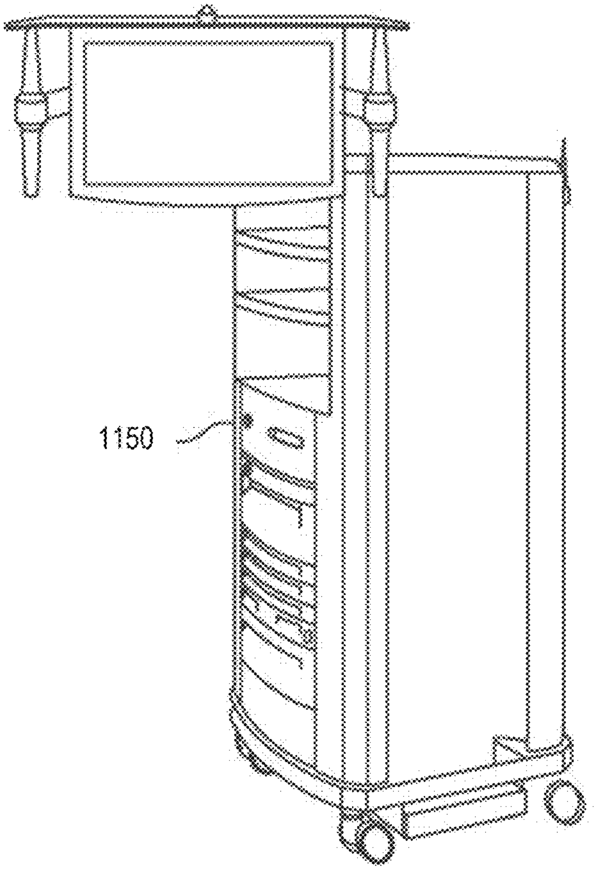
FIG. 3

LOW-FRICTION MEDICAL TOOLS HAVING ROLLER-ASSISTED TENSION MEMBERS

CROSS-REFERENCE TO RELATED APPLICATIONS

This patent application is a continuation of U.S. patent application Ser. No. 18/640,575 (filed Apr. 19, 2024) (entitled "LOW-FRICTION MEDICAL TOOLS HAVING ROLLER-ASSISTED TENSION MEMBERS"), which is a continuation of U.S. patent application Ser. No. 16/971,974 (filed Aug. 21, 2020) (entitled "LOW-FRICTION MEDICAL TOOLS HAVING ROLLER-ASSISTED TENSION MEMBERS"), which is a U.S. national stage filing under 35 U.S.C. § 371 of International Application No. PCT/US2019/020651 (filed Mar. 5, 2019) (entitled "LOW-FRICTION MEDICAL TOOLS HAVING ROLLER-ASSISTED TENSION MEMBERS"), which claims priority to and the filing date benefit of U.S. Provisional Patent Application No. 62/639,628 (filed Mar. 7, 2018) (entitled "LOW-FRICTION MEDICAL TOOLS HAVING ROLLER-ASSISTED TENSION MEMBERS"), each of which is incorporated herein by reference in its entirety.

BACKGROUND

The embodiments described herein relate to grasping tools, more specifically to medical devices, and still more specifically to endoscopic tools. More particularly, the embodiments described herein relate to low-friction tools and devices that include roller-assisted tension members that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include tension members (e.g., cables, tension bands) that extend through the main tube of the instrument and that connect the wrist mechanism to a transmission or actuator (also referred to herein as a backend mechanism). The backend mechanism moves the cables to operate the wrist mechanism. For robotic or teleoperated systems, the backend mechanism is motor driven and can be operably coupled to a processing system to provide a user interface for a doctor to control the instrument.

Patients benefit from continual efforts to improve the effectiveness of MIS methods and tools. For example, reducing the size and/or the operating footprint of the main tube and wrist mechanism can allow for smaller entry incisions, thereby reducing the negative effects of surgery, such as pain, scarring, and undesirable healing time. But, producing small diameter medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, some medical instruments have end effectors that require electrical energy for clinical functions such as desiccation, hemostasis, cutting, dissection, fulguration, incisions, tissue destruction, cauterizing, and vessel sealing. Accordingly, known instruments include one more conductors routed through the wrist mechanism to the portion of an end effector to be energized. Fitting all the components of the wrist mechanism, drive cables, and conductive wires into a small diameter, for example, less than about 10 mm, while preserving the necessary strength and function of these components can be difficult.

In addition to reducing the size of instrument, it is also desirable to develop low-cost instruments that are effectively disposable (i.e., that are intended for a single use only at an economic cost). With such instruments, each MIS procedure can be performed with a new, sterilized instrument, which eliminates cumbersome and expensive instrument reuse sterilization procedures. Many current instrument designs are expensive to produce, however, and so for economy these instruments undergo sterile reprocessing for use during multiple surgical procedures. In part, the cost of these instruments may be due to multiple-strand tungsten cables and hypotube portions to withstand the operating loads.

Thus, a need exists for improved endoscopic tools, including improved wrist mechanisms having reduced size, reduced part count, lower cost of materials, and increased strength tension members operating with low friction during use.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, a low-friction medical device includes a first link, a second link, a roller and a tension member. The first link is coupled to an instrument shaft and the second link has a proximal end portion and a distal end portion. The proximal end portion of the second link is rotatably coupled to the distal end portion of the first link. The second link is rotatable relative to the first link about a first axis. The distal end portion of the second link is rotatably coupled to a tool member that is rotatable relative to the second link about a second axis. A curved guide path is defined within the second link and the tension member extends through the curved guide path from the first link to tool member. The roller is coupled to the second link and has a roller surface aligned with a portion of the curved guide path. When the second link is in a first orientation with respect to the first link, the roller surface contacts a portion of the tension member in the curved guide path and rotates when tension is applied to the tension member.

In some embodiments, the second link includes a curved guide surface aligned with the portion of the guide path. In some embodiments, the tension member is wrapped about a pulley portion of the tool member, the pulley portion and the guide surface arranged such that the tension member has a small fleet angle. In some embodiments, the fleet angle is less than 10 degrees. In some embodiments, a tangent line to the roller surface is tangent to the curved guide path. In some embodiments, the curved guide surface is a first guide surface and the second link defines a pocket that separates the first guide surface from a second guide surface, and the roller is rotatably coupled within the pocket. In some embodiments, the first portion of the tension member is spaced apart from the roller surface when the second link is in a second orientation relative to the first link. In some embodiments, a pulley is coupled to the second link and the first portion of the tension member is spaced apart from the pulley when the second link is in the first orientation relative to the first link. The first portion of the tension member is in contact with the pulley when the second link is in the second orientation relative to the first link.

Other medical devices, related components, medical device systems and/or methods according to embodiments will be or become apparent to one with skill in the art upon review of the following drawings and detailed description. It is intended that all such additional medical devices, related components, medical device systems and/or methods included within this description, be within the scope of this disclosure.

BRIEF DESCRIPTION OF THE DRAWINGS

FIG. 2 is a perspective view of a user control console of the minimally invasive tele-operated surgery system shown in FIG. 1.

FIG. 3 is a perspective view of an optional auxiliary unit of the minimally invasive tele-operated surgery system shown in FIG. 1.

DETAILED DESCRIPTION

Figure 1:
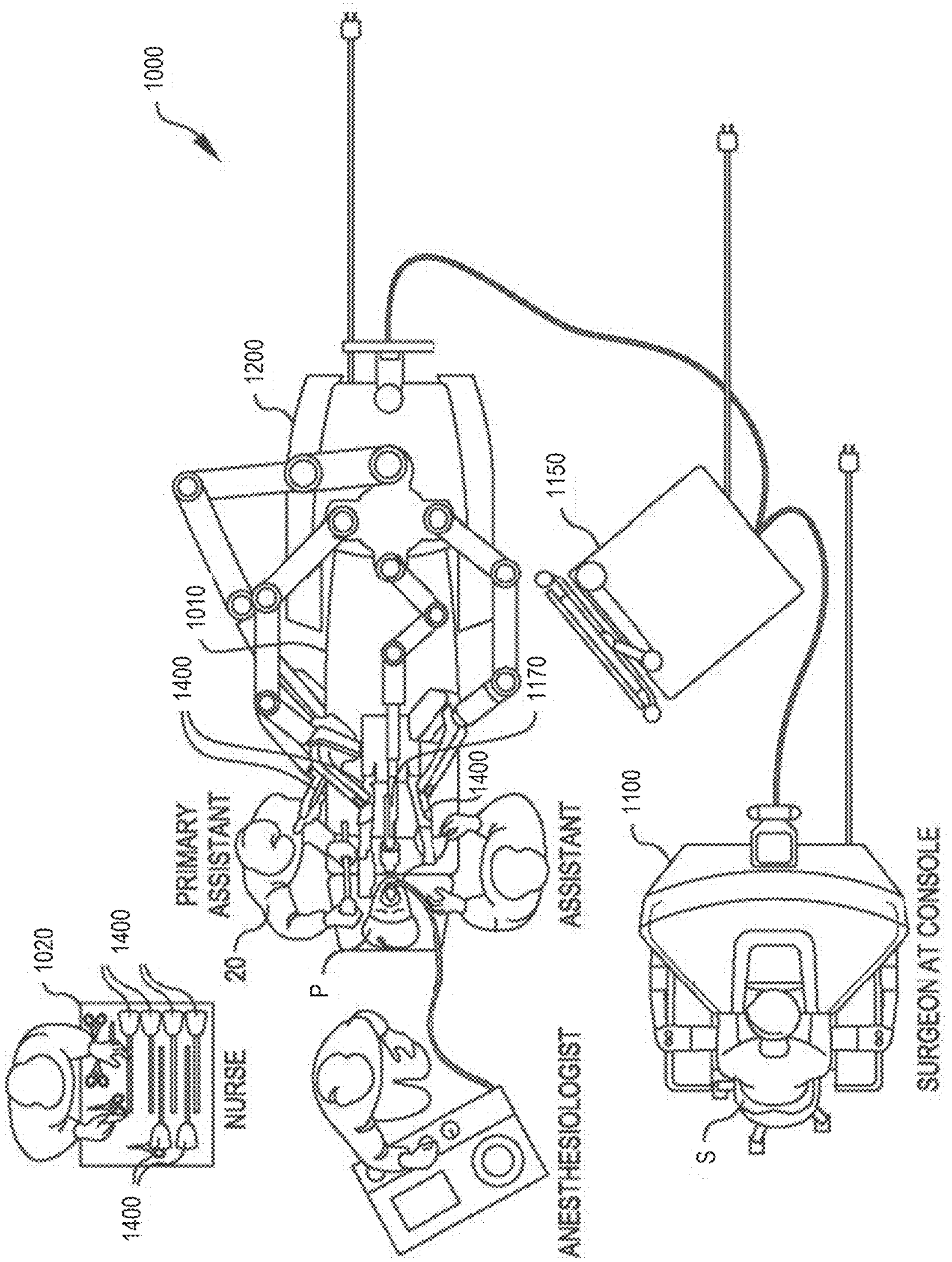
FIG. 1 is a plan view of a minimally invasive teleoperated medical device according to an embodiment, being used to perform a medical procedure such as surgery.

The embodiments described herein can advantageously be used in a wide variety of grasping, cutting, and manipulating operations associated with minimally invasive surgery. In particular, the instruments described herein can be low-cost, disposable instruments that facilitate being used for only one procedure. As described herein, the instruments include one or more cables (which act as tension members) that can be moved to actuate the end effector with multiple degrees of freedom. Moreover, the cables can include regions having a larger cross-sectional area to promote increased strength, or can be twisted to allow efficient routing within a miniaturized wrist assembly.

In some embodiments, a medical device includes a first link, a second link, a roller and a tension member. The first link is coupled to an instrument shaft and the second link has a proximal end portion and a distal end portion. The proximal end portion of the second link is rotatably coupled to the distal end portion of the first link. The second link is rotatable relative to the first link about a first axis. The distal end portion of the second link is rotatably coupled to a tool member that is rotatable relative to the second link about a second axis. A curved guide path is defined within the second link, and the second link includes a guide surface. The roller is coupled to the second link and has a roller surface. The roller surface and the guide surface are each aligned with a portion of the curved guide path. A proximal end portion of the tension member is disposed within the curved guide path, and is coupled to the tool member. The second link is rotatable relative to the first link about the first axis when the distal end portion of the tension member is moved.

In some embodiments, a tangent line to the roller surface is tangent to the curved guide path. In some embodiments, the curved guide surface is a first guide surface and the second link defines a pocket that separates the first guide surface from a second guide surface. The roller is rotatably coupled within the pocket. The first portion of the tension member is in contact with the first guide surface, the roller surface of the roller, and the second guide surface when the second link is in a first orientation relative to the first link. In some embodiments, the first portion of the tension member is spaced apart from the roller surface when the second link is in a second orientation relative to the first link. In some embodiments, the medical device includes a pulley coupled to the second link, the pulley arranged such that the first portion of the tension member is spaced apart from the pulley when the second link is in the first orientation relative to the first link. The first portion of the tension member is in contact with the pulley when the second link is in the second orientation relative to the first link. In some embodiments, the second portion of the tension member is wrapped about a pulley portion of the tool member and the tension member defines a fleet angle between the pulley coupled to the second link and the pulley portion of the tool member. In some embodiments, the fleet angle is less than 10 degrees.

In some embodiments, the curved guide path has a guide path radius of curvature that is greater than a radius of the roller. In some embodiments, the roller rotates relative to the second link when the tension member is moved. In some embodiments, the curved guide path is offset from a center line of the second link such that the second link rotates relative to the first link about the first axis when the tension member is moved. In some embodiments, the tension member is any one of a cable or a band. In some embodiments, the roller is coupled to the second link by a pin. In some embodiments, the roller is a ball captively coupled within the pocket defined by the second link.

In some embodiments, the tool member has a pulley portion coupled to the distal end portion of the second link by a pin. The second portion of the cable is wrapped about the pulley portion offset from the pin such that the tool member rotates relative to the second link about the second axis when the cable is moved. The cable defines a fleet angle between the curved guide surface of the second link and the pulley portion of the tool member. In some embodiments, the fleet angle is less than 10 degrees.

In some embodiments, the curved guide surface of the second link is a first guide surface, the roller is a first roller, the roller surface is a first roller surface, the curved guide path is a first curved guide path, the tension member is a first cable, and the apparatus further includes a second roller coupled to the second link. A second roller surface of the roller and a second guide surface define a second curved guide path. A second cable has a first portion and a second portion. The first portion of the second cable is within the second curved guide path and coupled to the tool member.

In some embodiments, a medical device includes a first link, a second link, a roller and a tension member. The first link is coupled to an instrument shaft and the second link has a proximal end portion and a distal end portion. The proximal end portion of the second link is rotatably coupled to the first link. The second link is rotatable relative to the first link about a first axis. The distal end portion of the second link is rotatably coupled to a tool member that is rotatable relative to the second link about a second axis. The second link includes a first guide surface and a second guide surface. The roller is coupled to the second link between the first guide surface and the second guide surface. The tension member has a first portion and a second portion. The first portion is in contact with the first guide surface, the roller, and the second guide surface when the second link is in a first orientation relative to the first link. The tension member is spaced apart from the roller when the second link is in a second orientation relative to the first link. The second portion of the tension member is coupled to the tool member. The tool member is rotatable relative to the second link about the second axis when the distal end portion of the tension member is moved.

In some embodiments, a medical device includes a first link, a second link, a roller, a pulley, and a tension member. The first link is coupled to an instrument shaft and the second link has a proximal end portion and a distal end portion. The proximal end portion of the second link is rotatably coupled to the first link. The second link is rotatable relative to the first link about a first axis. The distal end portion of the second link is rotatably coupled to a tool member that is rotatable relative to the second link about a second axis. The second link includes a guide surface. The roller and the pulley are each coupled to the second link. The tension member has a first portion and a second portion. The first portion is in contact with the roller and spaced apart from the pulley when the second link is in a first orientation relative to the first link. The first portion of the tension member is spaced apart from the roller and is in contact with the pulley when the second link is in a second orientation relative to the first link. The second portion of the tension member is coupled to the tool member. The tool member is rotatable relative to the second link about the second axis when the distal end portion of the tension member is moved.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100. An image of the surgical site is obtained by an endoscope 1170, such as a stereoscopic endoscope, which can be manipulated by the patient-side cart 1200 to orient the endoscope 1170. The electronics cart 1150 can be used to process the images of the surgical site for subsequent display to the Surgeon S through the surgeon's console 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the patient-side cart 1200 and replaces it with another instrument 1400 from a tray 1020 in the operating room. Although shown as being used with the instruments 1400, any of the instruments described herein can be used with the MIRS 1000.

FIG. 2 is a perspective view of the control unit 1100. The surgeon's console 1100 includes a left eye display 1112 and a right eye display 1114 for presenting the surgeon S with a coordinated stereo view of the surgical site that enables depth perception. The surgeon's console 1100 further includes one or more input control devices 1116, which in turn cause the patient-side cart 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the surgeon's console 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The surgeon's console 1100 is shown in FIG. 1 as being in the same room as the patient so that the surgeon S can directly monitor the procedure, be physically present if necessary, and speak to an assistant directly rather than over the telephone or other communication medium. In other embodiments, however, the surgeon's console 1100 and the surgeon S can be in a different room, a completely different building, or other remote location from the patient allowing for remote surgical procedures.

FIG. 3 is a perspective view of the electronics cart 1150. The electronics cart 1150 can be coupled with the endoscope 1170, and can include one or more processors to process captured images for subsequent display, such as via the surgeon's console 1100, or on another suitable display located locally and/or remotely. For example, where a stereoscopic endoscope is used, the electronics cart 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
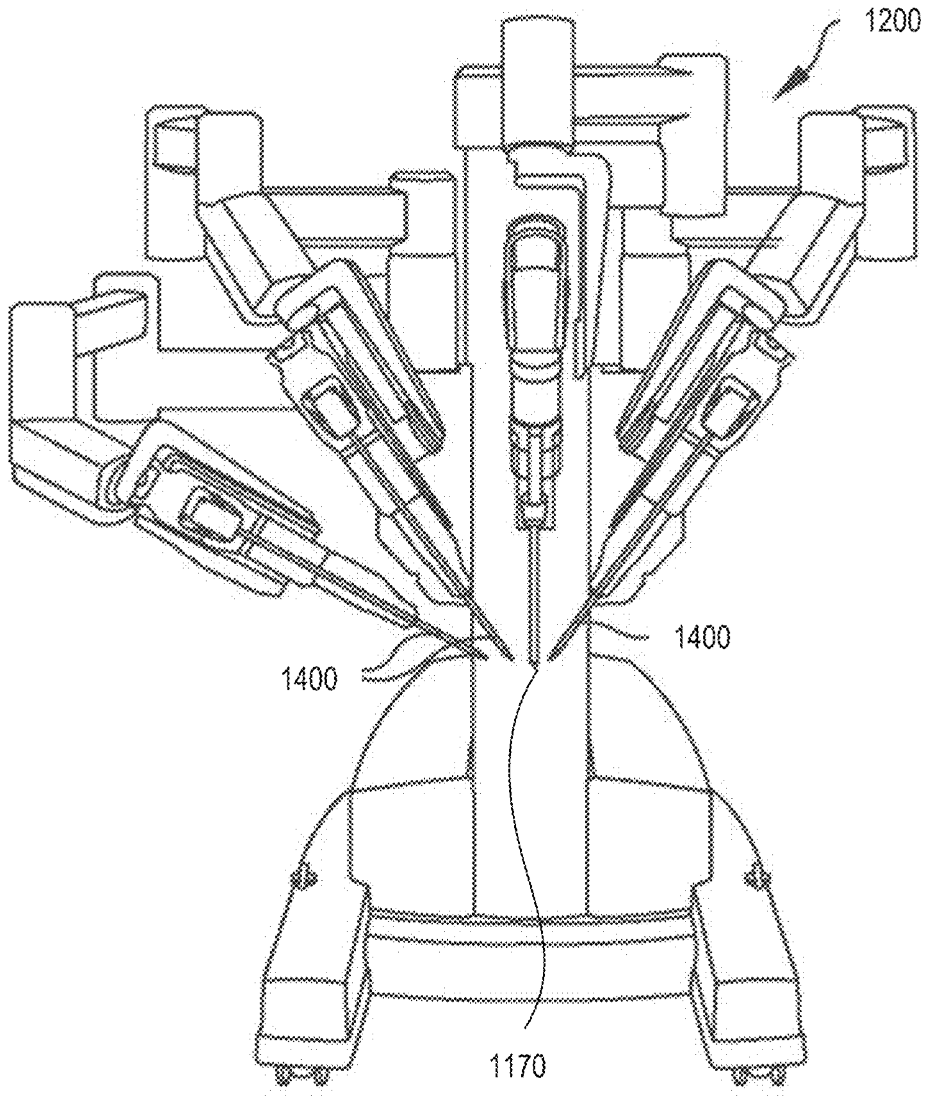
FIG. 4 is a front view of a manipulator unit, including a plurality of instruments, of the minimally invasive tele-operated surgery system shown in FIG. 1.

FIG. 4 shows a front perspective view of the patient-side cart 1200. The patient-side cart 1200 includes the components (e.g., arms, linkages, motors, sensors, and the like) to provide for the manipulation of the instruments 1400 and the imaging device 1170, such as a stereoscopic endoscope, used for the capture of images of the site of the procedure. Specifically, the instruments 1400 and the imaging device 1170 can be manipulated by teleoperated mechanisms having a number of joints. Moreover, the instruments 1400 and the imaging device 1170 are positioned and manipulated through incisions or natural orifices in the patient P in a manner such that a kinematic remote center of motion is maintained at the incision or orifice. In this manner, the incision size can be minimized.

Figure 5:
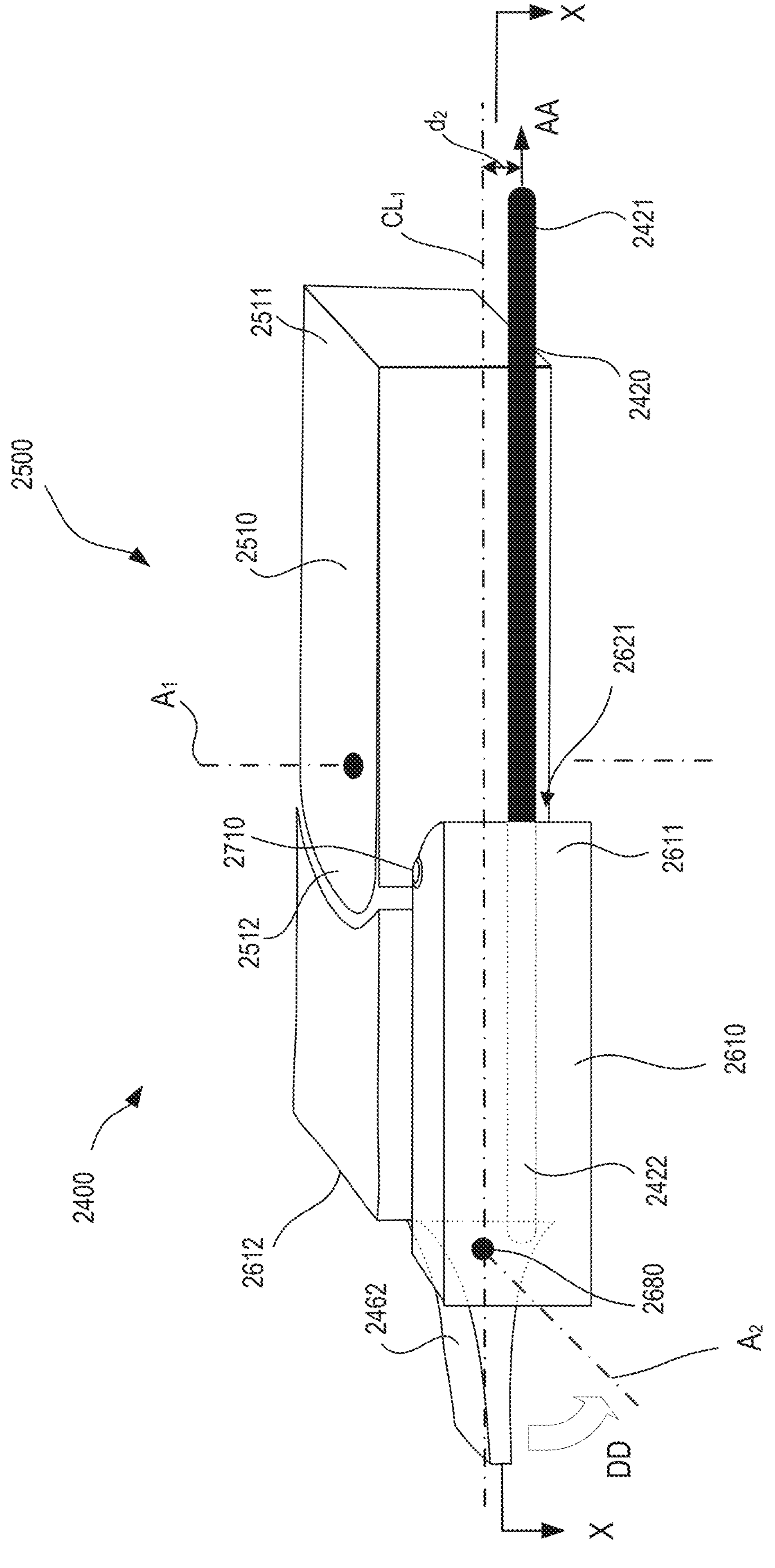
FIG. 5 is a diagrammatic perspective view of a portion of an instrument of a surgery system in a first position, according to an embodiment.
Figure 6A:
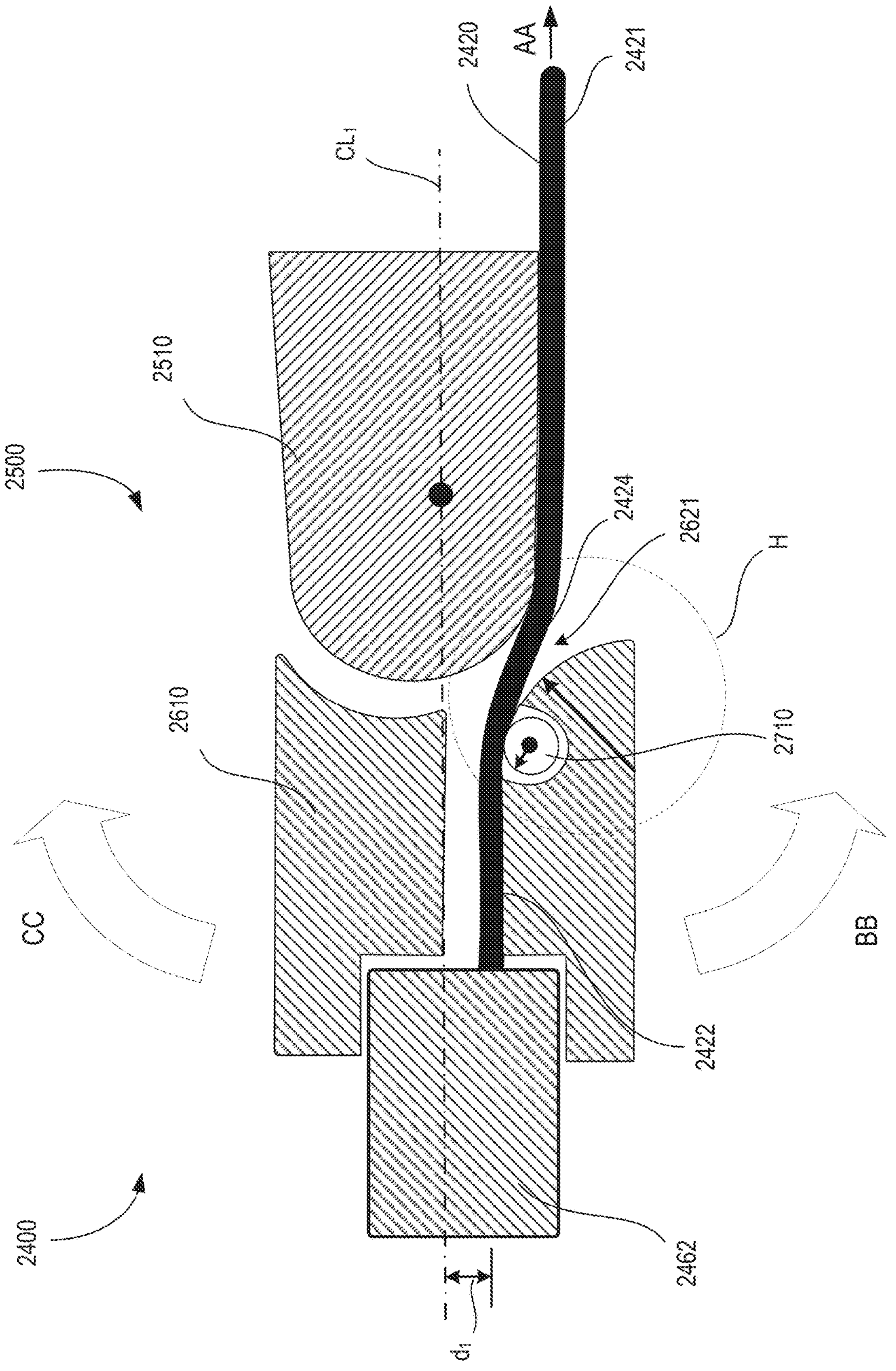
FIG. 6A is a diagrammatic top view of the portion of the instrument shown in FIG. 5 in the first orientation.
Figure 6B:
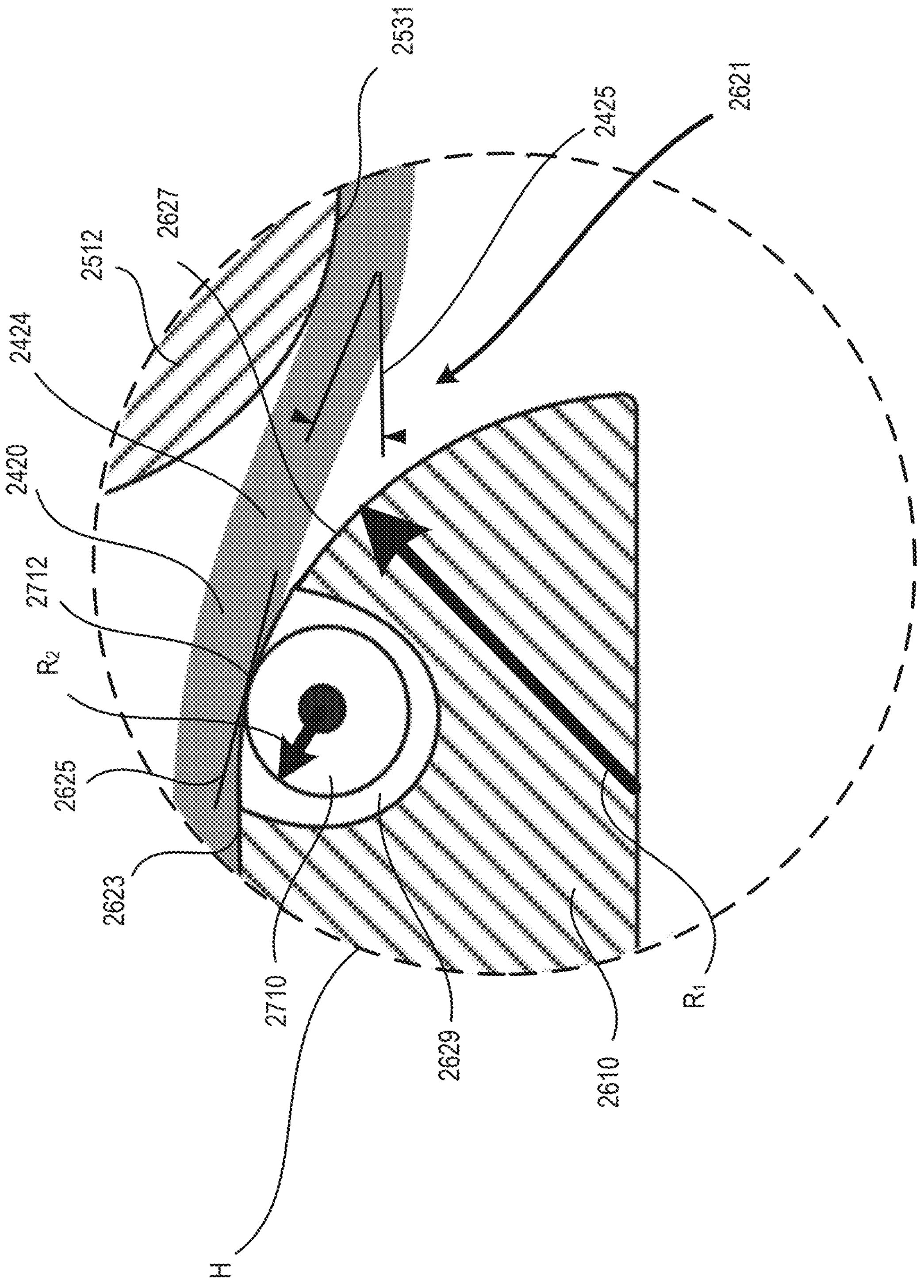
FIG. 6B is an enlarged view of a portion of the instrument shown in FIG. 5 by the region H shown in FIG. 6A.
Figure 7A:
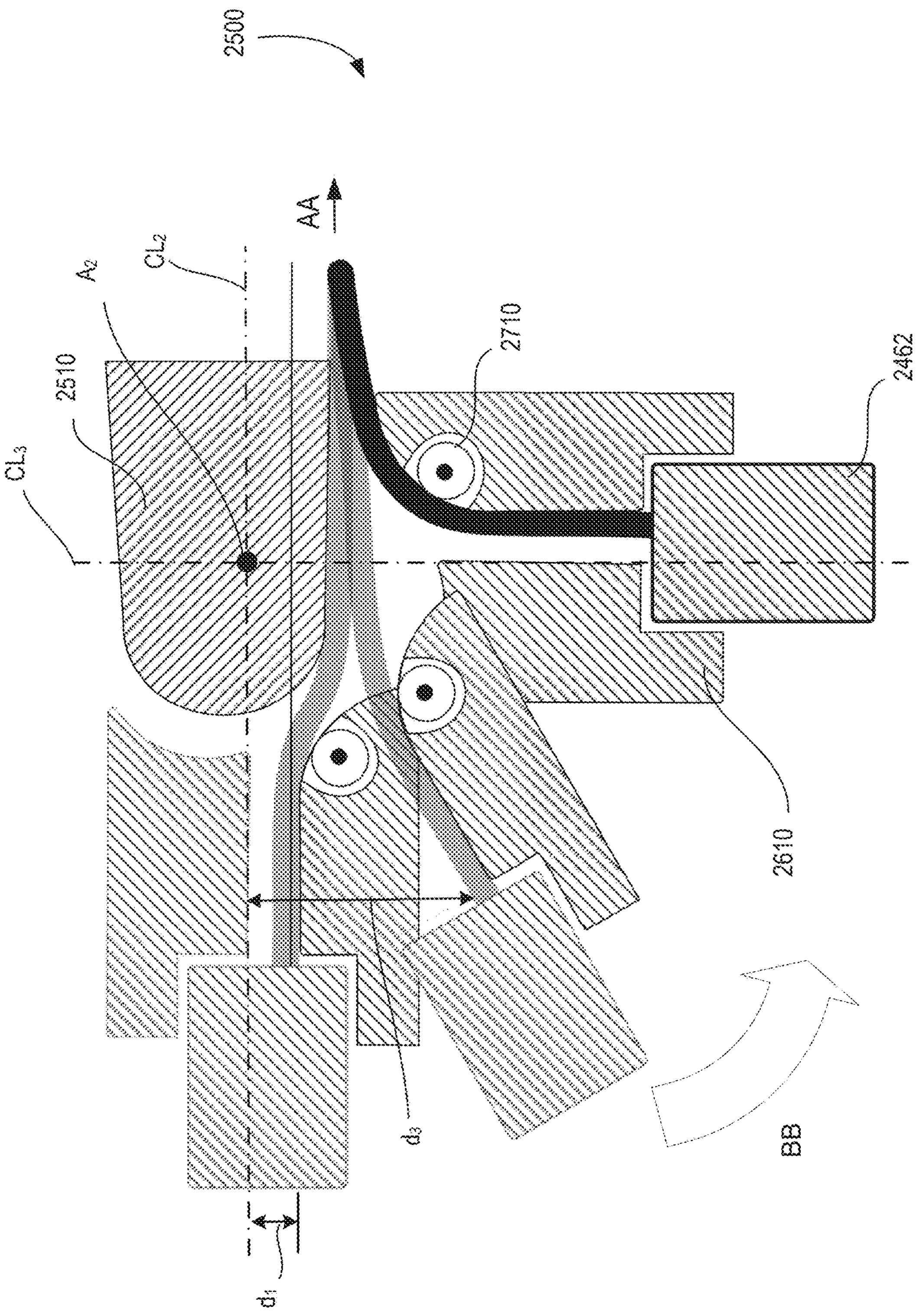
FIGS. 7A and 7B are diagrammatic top views of the portion of the instrument shown in FIG. 5 in a second orientation (FIG. 7A), and in a third orientation (FIG. 7B).
Figure 7B:
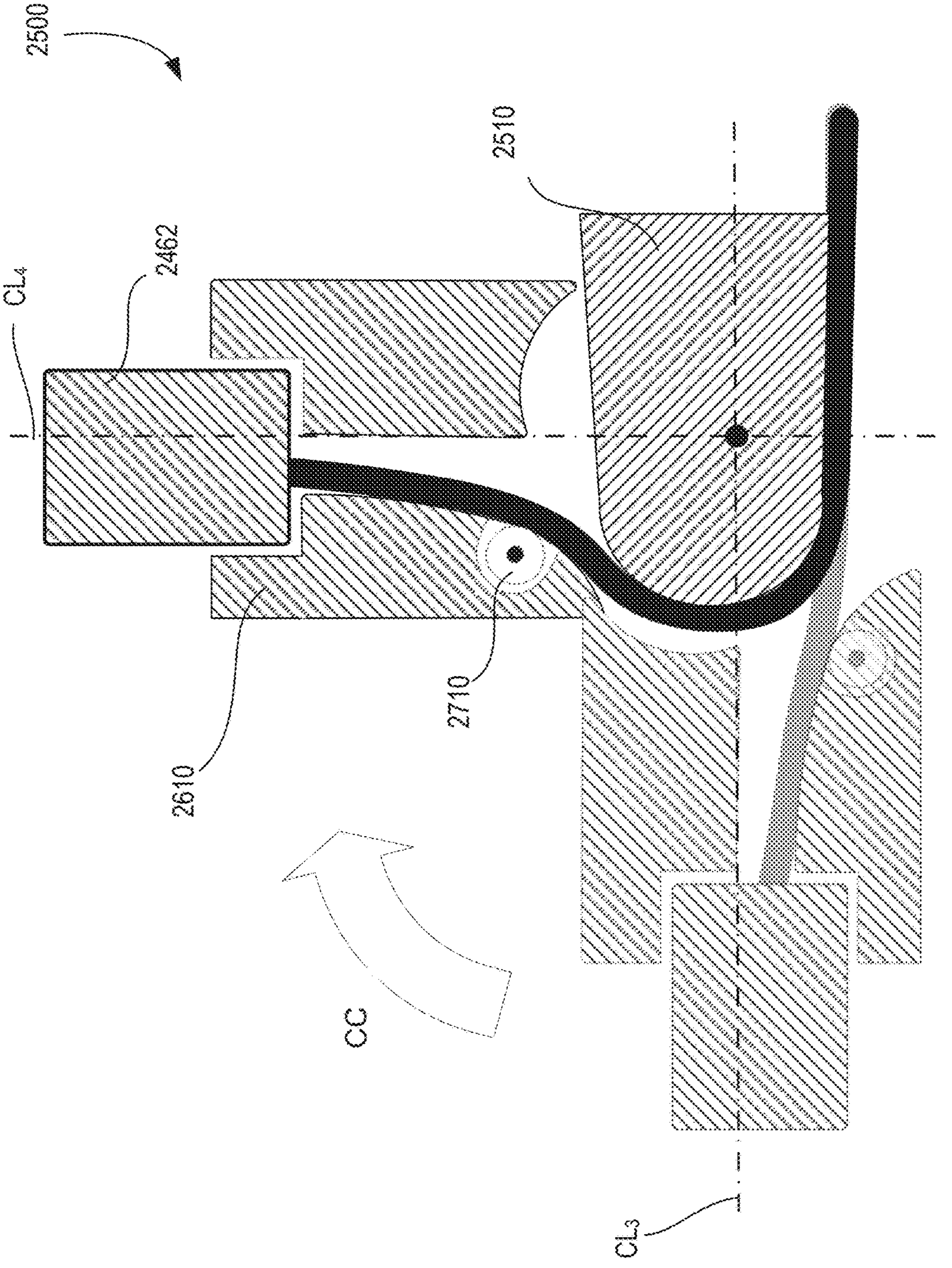

FIGS. 5, 6A, 6B, 7A and 7B are diagrammatic illustrations of various portions of an instrument 2400, according to an embodiment. In some embodiments, the instrument 2400 or any of the components therein are optionally parts of a surgical system that performs minimally invasive surgical procedures, and which can include a patient-side cart, a series of kinematic linkages, a series of cannulas, or the like. The instrument 2400 (and any of the instruments described herein) can be used in any suitable surgical system, such as the MIRS system 1000 shown and described above. The instrument 2400 includes a wrist assembly 2500, a cable 2420 (which acts as a tension member), and a tool member 2462. As described herein, the instrument 2400 is configured such that movement of the cable 2420 produces movement of the wrist assembly 2500 (as shown in FIGS. 7A and 7B), movement of the tool member 2462 (as illustrated in FIG. 5), or both movement of the wrist assembly 2500 and movement of the tool member 2462.

The wrist assembly 2500 includes a proximal first link 2510, a distal second link 2610, and a roller 2710 coupled to the distal second link 2610. The first link 2510 has a proximal end portion 2511 and a distal end portion 2512. The proximal end portion 2511 is coupled to an instrument shaft (not shown). Although the instrument shaft is not shown in FIGS. 5-7B, the proximal end portion 2511 can be coupled to any suitable instrument shaft, such as the instrument shaft 4410 shown and described herein. Moreover, the proximal end portion 2511 of the first link 2510 can be coupled to the instrument shaft via any suitable mechanism, such as welding, interference fit, adhesive, etc. As described below, the distal end portion 2512 is rotatably coupled to the second link 2610. In this manner, the first link 2510 and the second link 2610 form the wrist assembly 2500 having a first axis of rotation $A_1$ (which functions as a pitch axis; the term pitch is arbitrary) about which the second link can rotate relative to the first link.

The second link 2610 has a proximal end portion 2611 and a distal end portion 2612. As described above, the proximal end portion 2611 is rotatably coupled to the distal end portion 2512 of the first link 2510 to form a wrist joint. For example, in some embodiments, the proximal end portion 2611 can be coupled to the distal end portion 2512 via a pinned joint, such as the pinned joint between the proximal clevis 220 and the distal clevis 230 shown and described in U.S. Pat. No. 8,821,480 B2 (filed Jul. 16, 2008), entitled "Four-Cable Wrist with Solid Surface Cable Channels," which is incorporated herein by reference in its entirety. In other embodiments, the proximal end portion 2611 can be coupled to the distal end portion 2512 via mating disc surfaces, such as the types shown and described in U.S. Patent Application Pub. No. US 2017/0120457 A1 (filed Feb. 20, 2015), entitled "Mechanical Wrist Joints with Enhanced Range of Motion, and Related Devices and Methods," which is incorporated herein by reference in its entirety.

The distal end portion 2612 of the second link 2610 includes a connector 2680 that is coupled to the tool member 2462 such that the tool member 2462 can rotate relative to the wrist assembly 2500 about a second axis of rotation $A_2$. As shown in FIG. 5, the second axis of rotation $A_2$ (also referred to as the yaw axis or the grip axis) is non-parallel to the first axis of rotation $A_1$. As described herein, axis $A_2$ functions both as a yaw axis (the term yaw is arbitrary) as the tool member 2462 rotates together with another tool member (not shown, but a second tool member can optionally be included in the instrument 2400) and as a grip axis as the tool member rotate in opposition to another tool member (not shown). Thus, the instrument 2400 provides for up to three degrees of freedom (i.e., a pitch rotation about the first axis of rotation $A_1$, a yaw rotation about the second axis of rotation $A_2$, and a grip motion about the second axis of rotation $A_2$). Although the second axis of rotation $A_2$ is shown as being normal to the first axis of rotation $A_1$, in other embodiments, the second axis of rotation $A_2$ can be offset from the first axis of rotation $A_1$ by any suitable angle. The connector can be any suitable connector to rotatably couple the tool member 2462 to the second link 2610 to form a tool joint. For example, in some embodiments, the connector 2680 can include a clevis and a pin, such as the pinned joints shown and described in U.S. Pat. No. 9,204,923, entitled "Medical Instrument Electronically Energized Using Drive Cables," which is incorporated herein by reference in its entirety. In other embodiments, the connector 2680 can include a compliant mechanism, such as the compliant mechanisms shown and described in International Publication No. WO 2016/123139 A2 (filed Jan. 26, 2016), entitled "Rolling-Contact Joint Mechanisms and Methods," which is incorporated herein by reference in its entirety.

Referring to FIGS. 6A and 6B, a curved guide path 2621 is defined within the second link 2610, and the second link includes a first guide surface 2623. The roller 2710 is coupled to the second link and includes a roller surface 2712. The roller surface 2712 and the first guide surface 2623 are each aligned with a portion of the curved guide path 2621, such that a tangent line 2625 of the roller surface 2710 is also tangent to the curved guide path. The second link 2610 further includes a second guide surface 2627 and defines a pocket 2629 that separates the first guide surface 2623 and the second guide surface 2627. The roller 2710 is rotatably coupled within the pocket 2629. The distal end portion 2512 of the first link 2510 includes a proximal guide surface 2531.

The cable 2420 has a proximal end portion 2421, a distal end portion 2422 coupled to the tool member 2462, and a transition portion 2424 disposed between the proximal end portion and the distal end portion. The first guide surface 2623, the roller surface 2712 and the proximal guide surface 2531 of the first link 2510 contact the transition portion 2424 of the cable when the second link 2610 is in the first orientation shown in FIGS. 6A and 6B. Although shown as being in contact with the proximal guide surface 2531 of the first link 2510, in other embodiments, the transition portion 2424 of the cable 2420 is in contact with only the first guide surface 2623 and the roller surface 2712. The first guide surface 2623, the roller surface 2712, the proximal guide surface 2531, or any combination of these surfaces cooperate to guide the path of the cable 2420 to transition within the curved guide path 2621 between the path of the proximal end portion 2421 and the path of the distal end portion 2422 while in the first orientation shown in FIG. 6A. While in the first orientation shown in FIG. 6A, the path of the distal end portion 2422 is offset from the path of the proximal end portion 2421, and the transition portion 2424 provides an angled connection between the offset paths. Specifically, a fleet angle 2425 is defined between each of the paths of the proximal end portion 2421 and the distal end portion 2422 in the curved guide path 2621 and in the angled connection formed by the transition portion between the offset paths.

As described below in more detail, the offset tensile path arrangement with friction-reducing roller shown in FIGS. 6A and 6B provides several advantages over straight tensile path arrangements based on combinations of features including the fleet angle 2425. Such advantages can enhance pitch movements from the first orientation shown in FIG. 6A to the second orientation shown in FIG. 7A, and include the cable 2420 rotating away from frictional contact with the first link 2510 and the pitch moment arm increasing for tensile force applied through cable 2420 during pitch rotation. However, a large fleet angle 2425 can reduce the likelihood that cable length will be conserved and can permit portions of the cable 2420 to become slack during movements of the wrist assembly 2500 including the pitch movement shown in FIG. 7A. Slack portions of the cable 2420 can bind or get caught by components of the instrument 2400 during operation. Further, although a very small fleet angle 2425 can enhance cable length conservation and can reduce the likelihood of cable slack during movements of the wrist assembly 2500 including the pitch movement shown in FIG. 7A. A very small fleet angle 2425, however, can result in the cable 2420 being overly tight such that it limits the range of motion of the wrist assembly 2500.

Referring to FIG. 6B, the first guide surface 2623 and the proximal guide surface 2531 are advantageously configured to provide a fleet angle 2425 that conserves cable length while also guiding the cable 2420 during movements of the wrist assembly 2500 and tightly retaining the cable 2420 in the curved guide path 2621. As such, the transition cable portion 2424 is retained against the proximal guide surface 2531 of the first link 2510, as well as retained in contact against the first guide surface 2623 and the roller surface 2712. Roller 2710 is rotatably attached to the second link 2610 within the recessed pocket 2629 proximate the first guide surface 2623 such that its roller surface 2712 is aligned with a portion of the curved guide path 2621. As such, the roller 2710 has a radius of curvature $R_2$ that is smaller than a radius of curvature $R_1$ of the curved guide path 2621. Further, the roller surface 2712 is retained in contact with the transition portion 2424 of the cable when the second link is in the first orientation shown in FIGS. 6A and 6B.

The roller 2710 rotates when axial tension is applied to the cable 2420 along its longitudinal axis for pitch movements or movement of the tool member 2462 for yaw or grip movements. The rotation of the roller 2710 is based on contact with the cable 2420 at the roller surface 2712, and reduces friction that would otherwise occur when the cable slides against the surfaces of the second link 2610 when tension is applied to the cable for pitch, yaw, or grip movements. Further, the roller advantageously reduces friction at a position along the curved guide path 2621 proximate to the first guide surface 2623 where high tensile stress is applied when the cable is tightly retained within the curved guide path 2621. In some embodiments, such an advantageous configuration can be provided that results in a fleet angle 2425 of about 10 degrees or less. In some embodiments, the fleet angle 2425 can be between about 5 degrees and 10 degrees. In yet other embodiments, the fleet angle 2425 can be between about 5 degrees and 15 degrees. In some embodiments, the transition portion 2424 of the cable 2420 can also be in contact with the second contact surface 2627 when in the first orientation shown in FIGS. 6A and 6B. In some embodiments, the radius of curvature $R_1$ of the first and second guide surface 2623, 2627 is larger than a radius of curvature of the roller 2710. In some embodiments, the radius of curvature $R_1$ of the first and second guide surface 2623, 2627 is constant along both the first and second guide surfaces. In some embodiments, the radius of curvature $R_1$ changes along the first and second guide surfaces.

The offset tensile path arrangement with friction-reducing roller shown in FIGS. 6A and 6B provides several advantages over straight tensile path arrangements including size reduction, improved range of pitch motion with fewer components, reduction of overall components, reduction of the number of pulleys and supporting components for cables, reduction of cable friction and wear, and avoiding cable binding during high loads. The roller 2710 is located in the second link 2610 at a high load, high friction and/or high wear location along the curved guide path 2621. The arrangement shown in FIGS. 6A and 6B can provide a high range of pitch motions in a smaller sized wrist assembly 2500 than could be provided by a similar straight tensile path arrangement requiring additional components including multiple pulleys to provide the same high range of pitch motions. It is understood that multiple rollers (not shown) could be placed within the curved guide path 2621 at different targeted high load, high friction and/or high wear locations.

Referring to FIG. 5, the curved guide path 2621 (and therefore the transition portion 2424 of the cable 2420 therein) is offset from the second axis of rotation $A_2$ by a distance $d_2$. In this manner, application of a tension force on the cable 2420 (indicated by the proximally-directed arrow AA) produces a torque on the tool member 2462 about the second axis of rotation $A_2$, which results in rotation of the tool member 2462 relative to the second link 2610, as shown by the arrow DD in FIG. 5. Referring to FIG. 6A, the curved guide path 2621 (and therefore the transition portion 2424 of the cable 2420 therein) is offset from the longitudinal center line $CL_1$ of the first link 2510 and the first axis of rotation $A_1$ by a distance d1. In this manner, application of a tension force on the cable 2420 (indicated by the proximally-directed arrow AA in FIG. 6A) produces a torque about the first axis of rotation $A_1$, which results in rotation of the second link 2610 relative to the first link 2510, as shown by the downward arrow BB in FIG. 6A. As described below along with other embodiments herein, in some embodiments, a second cable (which also acts as a tension member) (not shown) can be similarly offset in an opposite direction from the longitudinal center line $CL_1$ of the first link 2510 and the first axis $A_1$. In this manner, application of a tension force on the second cable (not shown) produces a torque about the first axis of rotation $A_1$, which results in rotation of the second link 2610 relative to the first link 2510 in an opposite direction, as shown by the upward arrow CC in FIG. 7B.

As shown in FIGS. 7A & 7B, the second link 2610 defines a longitudinal center line $CL_3$ that intersects the first axis of rotation $A_1$. When the wrist assembly 2500 is in the first orientation (FIGS. 5, 6A and 6B), the longitudinal centerline $CL_2$ of the first link 2510 and the longitudinal center line $CL_3$ of the second link 2610 are collinear (and are collectively identified as $CL_1$ in FIG. 5). When the second link 2610 rotates relative to the first link 2510 (i.e., rotates in pitch), the longitudinal centerline $CL_2$ and the longitudinal center line $CL_3$ form a pitch angle.

Referring to FIG. 7A, high pitch motion of the second link 2610 about center line pivot point $A_2$ is shown that occurs as tensile force is longitudinally applied to cable 2420 in the direction AA. When the tensile force is applied along the cable 2420, the second link 2610 and the distal portion 2422 and the transition portion 2424 of the cable rotate in direction BB away from first link 2510. As such, cable 2420 is no longer in contact with the first link 2510 for the high pitch motion from the first orientation to a second orientation (at a pitch angle of about 45 degrees) and a third orientation shown in FIG. 7A (at a pitch angle of about 90 degrees), which significantly reduces the amount of frictional contact between the cable 2420 and components of the wrist assembly 2500 during the pitch movement. Further, as the second link 2610 and cable 2420 rotate away from the first link 2510, the distance d1 between the distal end portion 2426 and the rotation axis $A_2$ increases, which increases the moment arm for providing the high pitch motion.

Referring to FIG. 5, the tool member 2462 is coupled to the wrist assembly 2500 and rotates relative to the wrist assembly around the second axis of rotation $A_2$. In this manner, a distal portion (e.g., an engagement portion) of the tool member 2462 can engage or manipulate a target tissue during a surgical procedure. The tool member 2462 (or any of the tool members described herein) can be any suitable medical tool member. For example, in some embodiments, the tool member 2462 (or any of the tool members described herein) can include an engagement surface that functions as a gripper, cutter, tissue manipulator, or the like. In other embodiments, the tool member 2462 (or any of the tool members described herein) can be an energized tool member that is used for cauterization procedures. Although only one tool member 2462 is shown, in other embodiments, the instrument 2400 includes two moving tool members that cooperatively perform gripping or shearing functions. In this manner, the tool member 2462 can form a portion of an end effector for the surgical instrument 2400.

Referring again to FIG. 7A, the reduced amount of frictional contact between the cable 2420 and components of the wrist assembly 2500 when the instrument is in a high pitch orientation (e.g., the second orientation or the third orientation) allows the cable 2420 to be moved in the direction AA to move the tool member 2462 when in a high pitch orientation in an efficient manner and with a reduced likelihood that the cable 2420 will become bound. Similarly, the contact between the cable 2420 and the roller surface 2710 allows the roller 2710 to rotate when axial tension is applied to the cable 2420 for movement of the tool member 2462 relative to the second link 2610. Thus, as described above, the roller 2710 advantageously reduces friction at a position along the curved guide path 2621 where high tensile stress is applied when the when the instrument 2400 is at a high pitch orientation. This allows movement of the tool member 2462 throughout the range of pitch orientations (e.g., at pitch angles of between −90 degrees (FIG. 7B) and 90 degrees (FIG. 7A), at pitch angles of between −45 degrees and 45 degrees, at pitch angles of between −60 degrees and 60 degrees).

As described above, the cable 2420 has a proximal end portion 2421, a distal end portion 2422 and a transition portion 2424. The proximal end portion 2421 extends outside of the wrist assembly 2500, through the instrument shaft (not shown), and is coupled to an actuator (not shown). The actuator (which functions as a transmission) can move the proximal end portion 2421 of the cable by any suitable mechanism to produce a resulting movement (or force) at the distal end portion 2422 of the cable (as shown by arrow AA in FIGS. 5 and 6A). In some embodiments, the actuator of the instrument 2400 is motor driven, and is thus suitable for a robotic or tele-operated surgical system. The transition portion 2424 of the cable 2420 is disposed within the curved guide path 2621, and the distal end portion 2422 of the cable is coupled to the tool member 2462. In this manner, as described herein, movement of (or a force applied to) the cable 2420 can produce rotation of the tool member 2462, rotation of the second link 2610, or rotation of both the tool member 2462 and the second link 2610. The distal end portion 2422 of the cable 2420 can be coupled to the tool member 2462 by any suitable mechanism. For example, in some embodiments, the distal end portion 2422 can be coupled to the tool member 2462 by a pin or protrusion that engages (or is received within) a connection portion of the tool member 2462. In other embodiments, the distal end portion 2422 can be coupled to the tool member 2462 via an adhesive. In yet other embodiments, the distal end portion 2422 of the cable can be wrapped about a pulley portion of the tool member 2462.

In some embodiments, the cable 2420 can be made of Tungsten or stainless steel to provide sufficient strength, bendability and durability. In some embodiments, cables 2420 can be constructed from multiple braids of fine wire, to provide strength and resiliency. In some embodiments, cables 2420 can be made from 150 to 350 braids of 0.0007 inch to 0.001 inch diameter tungsten wire providing cables with outer diameters of 0.014 inches to 0.018 inches.

Although described as being cables, in other embodiments, the instrument 2400 can include any suitable tension member. For example, in some embodiments, the instrument 2400 (and any of the instruments described herein) can include a tension member having any suitable cross-sectional shape. For example, in some embodiments, the instrument 2400 (and any of the instruments described herein) can include a tension band, of the types shown and described in U.S. Patent Application No. 62/598,620 (filed Dec. 14, 2017), entitled "Medical Tools Having Tension Bands," which is incorporated herein by reference in its entirety. In some embodiments, such bands (and any of the tension members described herein) can have a trapezoidal shape. In other embodiments, such bands (and any of the tension members described herein) can include slightly curved surfaces. Moreover, such bands (and any of the tension members described herein) can be constructed from any suitable materials. For example, in some embodiments, such bands (and any of the tension members described herein) can be constructed from a series of laminates that are bonded together (e.g., via an adhesive). The laminates can be constructed from any suitable material, including tungsten, steel, or any suitable polymer.

In use, the distal end portion of the instrument 2400 provides for up to three degrees of freedom, and can be moved between multiple different configurations to perform a variety of surgical operations. For example, in some situations, movement of the distal end portion 2422 of the cable 2420, as shown by the arrow AA in FIG. 7A, can produce rotation of the second link 2610 about the pitch axis $A_1$ (as shown by the arrow BB in FIG. 7A). The amount of rotation, the force needed to produce the desired rotation, and the amount of movement of the cable 2420 can be controlled by, among other things, the offset distance d1 between the cable 2420 and the pitch axis $A_1$. For example, a greater offset distance d1 will produce a greater moment arm. The amount of rotation, the force needed to produce the desired rotation, and the amount of movement of the cable 2420 can be controlled by, among other things, the offset distance d2 between the cable 2420 and the yaw axis $A_2$. For example, a greater offset distance d2 will produce a greater moment arm.

Although the first link 2510 and the second link 2610 are shown as having a rectangular cross-sectional shape, in other embodiments, either the first link 2510, the second link 2610, or both the first link 2510 and the second link 2610 can have any suitable cross-sectional shape. For example, in some embodiment, either the first link 2510, the second link 2610, or both the first link 2510 and the second link 2610 can have substantially circular cross-sectional shape (i.e., the wrist assembly 2500 can be substantially cylindrical).

Figure 8A:
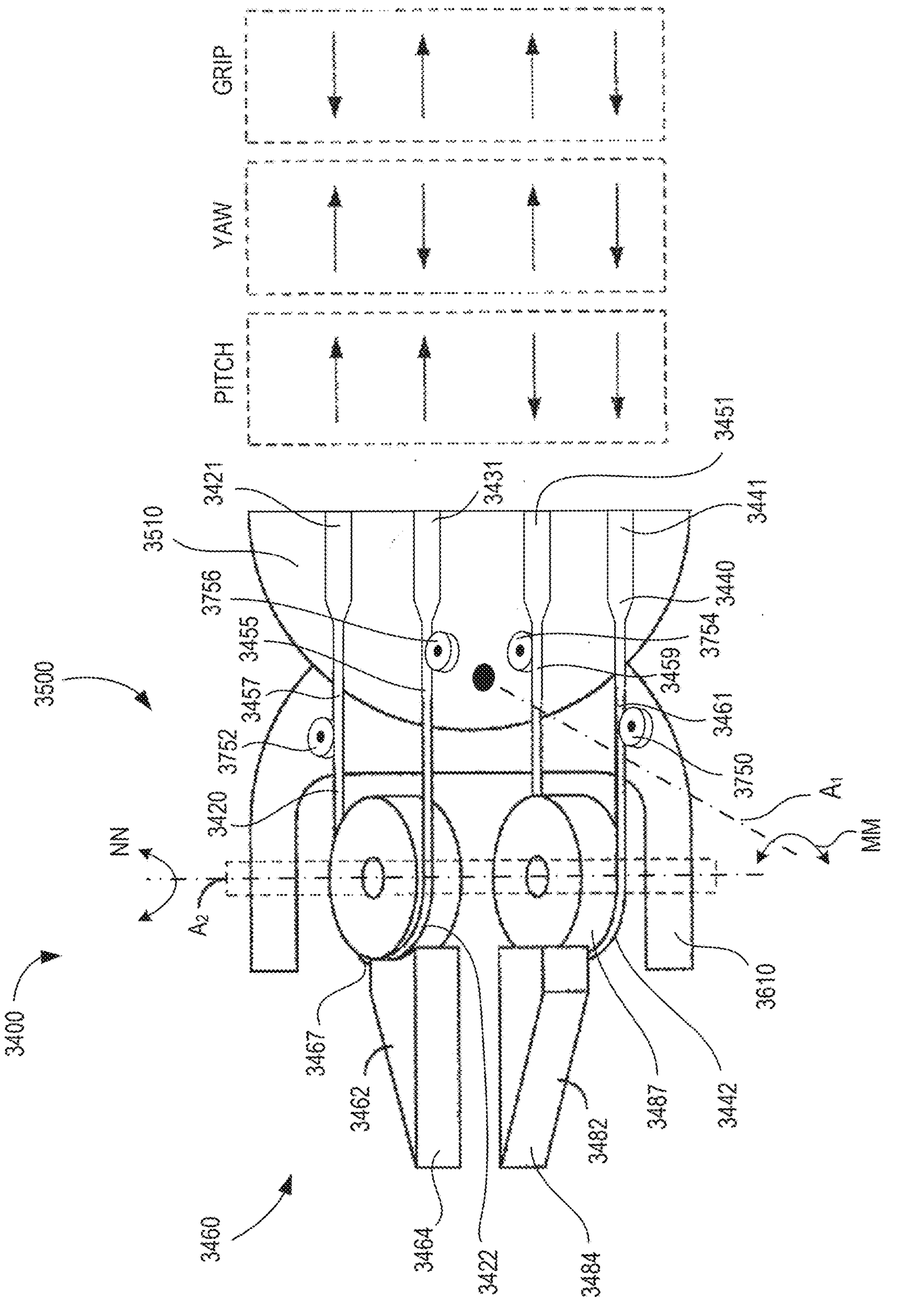
FIG. 8A is a diagrammatic illustration of a portion of an instrument of a surgery system, according to an embodiment.

Although the instrument 2400 is shown and described as including a single tool member 2462 and a single tension member (i.e., the cable 2420), in other embodiments, an instrument can include any suitable number of tension members or tool member. For example, in some embodiments, an instrument can include four tension members (or portions of tension members), and a wrist assembly can include at least one roller that reduces the friction of each of the four tension members. FIG. 8A is a schematic illustration of a portion of an instrument 3400, according to an embodiment. The instrument 3400 includes a wrist assembly 3500, a first tension member 3420, a second tension member 3440, and an end effector 3460. The instrument 3400 is configured such that movement of various portions of the first tension member 3420 and the second tension member 3440 can produce movement of the wrist assembly 3500 about the pitch axis $A_1$, movement of the end effector 3460 about the yaw axis $A_2$, gripping motion of the end effector 3460, or any combination of these motions.

The wrist assembly 3500 (which functions as a joint assembly) includes a first link 3510 and a second link 3610. The first link 3510 is coupled to an instrument shaft (not shown) of the types shown and described herein. The second link 3610 has a proximal end portion and a distal end portion. The proximal end portion is rotatably coupled to the first link 3510 to form the wrist assembly 3500 having a first axis of rotation $A_1$ (which functions as the pitch axis, the term pitch is arbitrary) about which the second link 3610 can rotate relative to the first link 3510. The wrist assembly 3500 can include any suitable coupling mechanism. For example, in some embodiments, the second link 3610 can be coupled to the first link 3510 via a pinned joint of the types shown and described herein. In other embodiments, the second link 3610 can be coupled to the first link 3510 via mating disc surfaces of the types shown and described herein.

The distal end portion of the second link 3610 is coupled to the end effector 3460. More specifically, the distal end portion of the second link 3610 is coupled to a pulley portion 3467 of a first tool member 3462 and a pulley portion 3487 of a second tool member 3482. This arrangement allows each of the tool member 3462 and the tool member 3482 to rotate relative to the wrist assembly 3500 about a second axis of rotation $A_2$. The second axis of rotation $A_2$ is non-parallel to the first axis of rotation $A_1$ and functions both as a yaw axis (the term yaw is arbitrary) as tool members rotate together and as a grip axis as tool members rotate in opposition to each other. Thus, the instrument 3400 provides for up to three degrees of freedom (i.e., a pitch motion about the first axis of rotation $A_1$, a yaw rotation about the second axis of rotation $A_2$, and a grip motion about the second axis of rotation $A_2$). Although the end effector 3460 is shown as being coupled to the second link 3610 via a pin connector, in other embodiments, the end effector 3460 can be coupled to the wrist assembly 3500 by any suitable mechanism.

The end effector includes the first tool member 3462 and the second tool member 3482. The first tool member 3462 includes a contact portion 3464 and a pulley portion 3467, and the second tool member 3482 includes a contact portion 3484 and a pulley portion 3487. The contact portion 3464 and the contact portion 3484 are each configured to engage or manipulate a target tissue during a surgical procedure. For example, in some embodiments, the contact portions can include an engagement surfaces that function as a gripper, cutter, tissue manipulator, or the like. In other embodiments, the contact portions can be an energized tool member that is used for cauterization procedures. As described above, the pulley portion 3467 and the pulley portion 3487 are each rotatably coupled to the second link 3610 such that the tool member 3462 can rotate relative to the wrist assembly 3500 via the second axis of rotation $A_2$. The pulley portions can include a contact surface about which the corresponding tension members (i.e., the first tension member 3420 and the second tension member 3440) are wrapped. The first tool member 3462 and the second tool member 3482 (or any of the tool members described herein) can be any suitable tool member of the types shown and described herein.

The first tension member 3420 (which can be a band or a cable) has a first proximal end portion 3421, a second proximal end portion 3431, and a distal end portion 3422. As shown, the distal end portion 3422 is wrapped about the pulley portion 3467 of the first tool member 3462. In this manner, the first proximal end portion 3421 and the second proximal end portion 3431 each extend through the first link 3510 and into the instrument shaft (not shown). Additionally, the first proximal end portion 3421 and the second proximal end portion 3431 are each coupled to an actuator (not shown) that can move each of the proximal end portions (as shown by the series of arrows labeled as PITCH, YAW, and GRIP). A first distal roller 3752 is rotatably attached to the second link 3610 adjacent to a first outer portion 3457 of the first tension member 3420 that extends between the first proximal end portion 3421 and the distal end portion 3422 of the first tension member when the wrist assembly 3500 is in a first orientation shown in FIG. 8A. An outer surface of the first distal roller 3752 contacts the first outer portion 3457 of the first tension member 3420 when the wrist assembly 3500 is in the first orientation. A first proximal roller 3756 is rotatably attached to the first link 3510 adjacent to a first inner portion 3455 of the first tension member 3420 that extends between the second proximal end portion 3431 and the distal end portion 3422 of the first tension member when the wrist assembly 3500 is in the first orientation shown in FIG. 8A. An outer surface of the first proximal roller 3756 contacts the first inner portion 3455 of the first tension member 3420 when the wrist assembly 3500 is in the first orientation.

The second tension member 3440 (which can be a band or a cable) has a third proximal end portion 3441, a fourth proximal end portion 3451, and a distal end portion 3442. As shown, the distal end portion 3442 is wrapped about the pulley portion 3487 of the second tool member 3482. In this manner, the third proximal end portion 3441 and the fourth proximal end portion 3451 each extend through the first link 3510 and into the instrument shaft (not shown). Additionally, the third proximal end portion 3441 and the fourth proximal end portion 3451 are each coupled to an actuator (not shown) that can move each of the proximal end portions (as shown by the series of arrows labeled as PITCH, YAW, and GRIP). A second proximal roller 3754 is rotatably attached to the first link 3510 adjacent to a second inner portion 3459 of the second tension member 3440 that extends between the third proximal end portion 3451 and the distal end portion 3442 of the second tension member when the wrist assembly 3500 is in the first orientation shown in FIG. 8A. An outer surface of the second proximal roller 3754 contacts the second inner portion 3459 of the second tension member 3440 when the wrist assembly 3500 is in the first orientation. A second distal roller 3750 is rotatably attached to the second link 3610 adjacent to a second inner portion 3459 of the second tension member 3440 that extends between the fourth proximal end portion 3441 and the distal end portion 3442 of the second tension member when the wrist assembly 3500 is in a first orientation shown in FIG. 8A. An outer surface of the second distal roller 3750 contacts the second outer portion 3461 of the second tension member 3440 when the wrist assembly 3500 is in the first orientation.

In some embodiments, the first tension member 3420 or the second tension member 3440 (or both) can be monolithically constructed such that the first proximal end portion, the second proximal end portion, and the distal end portion are all within a single element. In other embodiments, however, the first tension member 3420 or the second tension member 3440 (or both) can include multiple separately constructed components (e.g., the first proximal end portion 3421 can be separately constructed from the second proximal end portion 3431). Moreover, the first tension member 3420 or the second tension member 3440 (or both) can have any suitable shape as described herein. In some embodiments, the first tension member 3420 or the second tension member 3440 (or both) can have varying cross-sectional areas. In some embodiments, the first tension member 3420 or the second tension member 3440 (or both) can be constructed from a series of laminates that are bonded together (e.g., via an adhesive). The laminates can be constructed from any suitable material, including tungsten, steel, or any suitable polymer. In some embodiments, the first tension member 3420 and the second tension member 3440 can be constructed as steel cables.

Changing the pitch, yaw, or grip of the instrument 3400 generally requires movements or actions respectively applied to each of the four proximal end portions (the first proximal end portion 3421, the second proximal end portion 3431, the third proximal end portion 3441, and the fourth proximal end portion 3451). The movement of the tension member portions can generally be performed one at a time or simultaneously in any desired combination to change the pitch, yaw, and grip of instrument 3400. For example, pitch axis rotations rotate the second link 3610 about the first axis of rotation $A_1$ (pitch axis), as shown by the arrow MM. For clockwise rotation about the pitch axis $A_1$, the actuators (not shown) pull in (i.e., move proximally) identical lengths of the first proximal end portion 3421 and the second proximal end portion 3431 while releasing (i.e., allowing to move distally) the same lengths of the third proximal end portion 3441 and the fourth proximal end portion 3451. This is illustrated by the arrows labeled as PITCH.

The first proximal end portion 3421 and the second proximal end portion 3431 apply forces to the second link 3610 at moment arms defined by the curved guide paths through the wrist assembly 3500. Similarly stated, the first link 3510 and the second link 3610 can define one or more curved guide paths that are offset from the pitch axis $A_1$ to produce a torque about the pitch axis $A_1$. The curved guide paths can be any of the curved guide paths described herein (e.g., the curved guide paths shown and described in connection with the wrist assembly 2500 or the wrist assembly 4500). Similarly, for counterclockwise rotation of the second link 3610 about the pitch axis $A_1$, the actuators pull in (i.e., move proximally) identical lengths of the third proximal end portion 3441 and the fourth proximal end portion 3451 while releasing (i.e., allowing to move distally) the same lengths of the first proximal end portion 3421 and the second proximal end portion 3431.

Yaw rotations are the rotation of the first tool member 3462 and the second tool member 3482 about the second axis of rotation $A_2$ (yaw axis) in the same direction and through the same angle. In particular, when the actuators pull in (i.e., move proximally) a length of the first proximal end portion 3421 and release (i.e., allow to move distally) an equal length of the second proximal end portion 3431, the first tool member 3462 will rotate in a clockwise direction about the yaw axis $A_2$ (see the arrow NN). For this rotation, the curved guide path or pulley surface of the pulley portion 3467 defines the moment arm at which force transmitted via the first tension member 3420 is applied. The resulting torque causes the first tool member 3462 to rotate clockwise. During this movement, the first proximal end portion 3421 and the second proximal end portion 3431 each slide within the curved guide paths of the second link 3610. If, at the same time, the actuators pull in a length of the fourth proximal end portion 3451 and release the same length of the third proximal end portion 3441, the second tool member 3482 will rotate clockwise through an angle that is the same as the angle through which the first tool member 3462 rotates. Accordingly, the first tool member 3462 and the second tool member 3482 maintain their positions relative to each other and rotate as a unit through a yaw angle. Counterclockwise rotation of the end effector 3460 is similarly accomplished when the actuators pull in equal lengths of the second proximal end portion 3431 and the third proximal end portion 3441 while releasing the same lengths of the first proximal end portion 3421 and the fourth proximal end portion 3451. This is illustrated by the arrows labeled as YAW.

Grip rotations are rotations of the first tool member 3462 and the second tool member 3482 about the yaw axis $A_2$ in opposite directions and through the same angle. To open the grip of the end effector 3460, the actuators pull in equal lengths of the first proximal end portion 3421 and the third proximal end portion 3441 while releasing the same lengths of the second proximal end portion 3431 and the fourth proximal end portion 3451. This causes the first tool member 3562 to rotate in an opposite direction from the second tool member 3482. To close the grip of the end effector, the actuators pull in equal lengths of the second proximal end portion 3431 and the fourth proximal end portion 3451 while releasing the same lengths of the first proximal end portion 3421 and the third proximal end portion 3441. This causes the first tool member 3562 to rotate towards the second tool member 3482. When contact portion of the tool members come into contact, the tension in the second proximal end portion 3431 and the fourth proximal end portion 3451 can be kept greater than the tension in the first proximal end portion 3421 and the third proximal end portion 3441 to maintain the desired gripping forces.

The proximal rollers (first proximal roller 3756 and second proximal roller 3754) are each rotatably coupled to the first link 3510 on opposite sides of the pitch axis $A_1$ between the first tension member 3420 and the second tension member 3440. The outer surface of the first proximal roller 3756 contacts the first inner portion 3455 of the first tension member while in the orientation shown in FIG. 8A. Likewise, the outer surface of the second proximal roller 3754 contacts the second inner portion 3459 of the second tension member while in the orientation shown in FIG. 8A. As such, the outer surface of each of the proximal roller 3754, 3756 rotates along with corresponding movements of the first tension member 3420 and the second tension member 3440. As such, the proximal rollers 3754, 3756 maintain the inner portions (first inner portion 3457 and second inner portion 3459) of the first and second tension members 3420, 3440 in alignment with the instrument shaft regardless of the pitch, yaw and grip movements of the wrist assembly 3500, which prevents interfering contact between the first and second tension members 3420, 3440 and other objects from occurring during movements of the wrist assembly that can cause the tension members to bind or become entangled. Further, proximal rollers 3754, 3756 advantageously reduce friction at high tensile stress positions along the tension members 3420, 3440. In particular, each of the proximal rollers 3754, 3756 is located on the first link 3510 on opposite sides of the pitch pivot $A_1$, about which second link 3610 rotates for pitch movements. When high pitch movements are made, high tensile stresses are applied to the tension member 3420, 3440 located on the side opposite the direction of pitch rotation. The proximal rollers 3754, 3756 can reduce friction at the high tensile stress locations proximate the pitch pivot $A_1$, which can reduce wear on the tension member 3420, 3440 and enhance operation of the wrist assembly 3500.

The distal rollers (first distal roller 3752 and second distal roller 3750) are each rotatably coupled to the second link 3610 on opposite, outer portions of the second link 3610. The outer surface of the first distal roller 3752 contacts the first outer portion 3457 of the first tension member while in the orientation shown in FIG. 8A. Likewise, the outer surface of the second distal roller 3752 contacts the second outer portion 34561 of the second tension member while in the orientation shown in FIG. 8A. As such, the outer surface of each of the distal rollers 3752, 3750 rotate along with corresponding movements of the first tension member 3420 and the second tension member 3440. The distal rollers 3752, 3750 are coupled to the second link 3610 that rotates during pitch movements of the wrist assembly 3500. As such, the distal rollers 3752, 3750 guide the outer portions (first outer portion 3457 and second outer portion 3461) of the first and second tension members 3420, 3440 during pitch rotation movements to keep the first and second tension members 3420, 3440 properly positioned to avoid catching on objects during movements of the wrist assembly and binding or becoming tangled. Further, proximal rollers 3752, 3750 advantageously guide the paths of the first and second tension members 3420, 3440 throughout the range of motion for pitch movements with low friction.

The rollers 3750, 3752, 3754, and 3756 can be any suitable roller of the types shown and described herein. For example, in some embodiments, any of the rollers 3750, 3752, 3754, and 3756 can have a radius that is less than a radius of curvature of any of the guide paths defined within the wrist assembly 3500. Moreover, although the rollers 3750, 3752, 3754, and 3756 are shown and described as being in contact with their respective portions of the first tension member 3420 and the second tension member 3440, when the wrist assembly is in a second configuration, any of the rollers 3750, 3752, 3754, and 3756 can be spaced apart from their respective portions of the first tension member 3420 and the second tension member 3440.

Figure 8B:
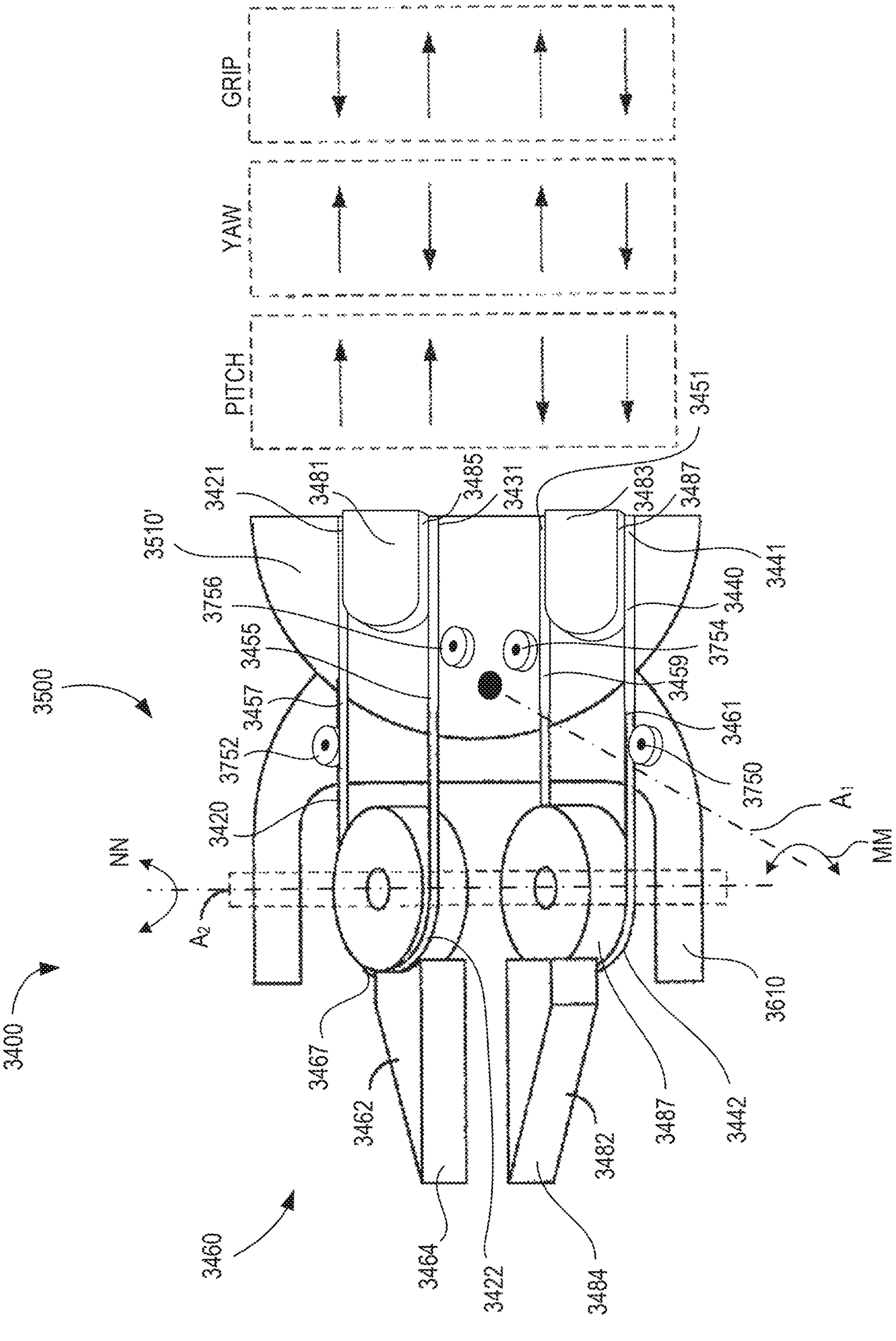
FIGS. 8B-8D are diagrammatic illustrations of a portion of an instrument system, according to embodiments.

The wrist assembly 3500 (and any of the wrist assemblies described herein) can include any suitable structure to define any suitable guide paths within which the tension members move. For example, referring to FIG. 8B, in some embodiments, the first link 3410' includes a first proximal guide spacer 3481 and a second proximal guide spacer 3483. The first proximal guide spacer 3481 is located between the first proximal end portion 3421 and the second proximal end portion 3431 of the first tension member 3420. The first proximal guide spacer 3481 includes side edge portions 3485 that are adjacent to each of the first proximal end portion 3421 and the second proximal end portion 3431. The second proximal guide spacer 3483 is located between the third proximal end portion 3441 and the fourth proximal end portion 3451 of the second tension member 3440. The second proximal guide spacer 3483 includes side edge portions 3487 that are adjacent to each of the third proximal end portion 3441 and the fourth proximal end portion 3451. The first and second proximal guide spacers 3481, 3483 guide the first and second tension members 3420, 3440 during operation to ensure proper alignment. Although the first proximal guide spacer 3481 and the second proximal guide spacer 3483 are shown as being included within the first link 3510', in other embodiments, the second link 3610 can also include any number of or arrangement of guide spacers.

Although the first proximal guide spacer 3481 and the second proximal guide spacer 3483 are shown as being stationary (i.e., non-moving) structures that define one or more guide paths, in other embodiments, a wrist assembly can include one or more rotating pulleys that, along with the rollers, define the guide paths within which the tension members move. For example, referring to FIG. 8C, in some embodiments, a first link 3410" includes a first proximal guide pulley 3491 and a second proximal guide pulley 3493. The first proximal guide pulley 3491 is located between the first proximal end portion 3421 and the second proximal end portion 3431 of the first tension member 3420. The first proximal guide pulley 3491 includes side edge portions 34895 that are adjacent to each of the first proximal end portion 3421 and the second proximal end portion 3431. The second proximal guide pulley 3493 is located between the third proximal end portion 3441 and the fourth proximal end portion 3451 of the second tension member 3440. The second proximal guide pulley 3493 includes side edge portions 3497 that are adjacent to each of the third proximal end portion 3441 and the fourth proximal end portion 3451. The first and second proximal guide pulleys 3491, 3493 guide the first and second tension members 3420, 3440 during operation to ensure proper alignment. The first and second tension members 3420, 3440 can advantageously wrap around distal portions of the first and second proximal guide pulleys 3491, 3493 during pitch rotations. In some embodiments, the first and second proximal guide pulleys 3491, 3493 can each include an upper and lower guide pulley that are each adjacent to a corresponding one of the first, second, third and fourth end portions 3421, 3431, 3441 and 3451 to reduce friction and independently rotate with movements of the corresponding end portion.

Figure 8C:
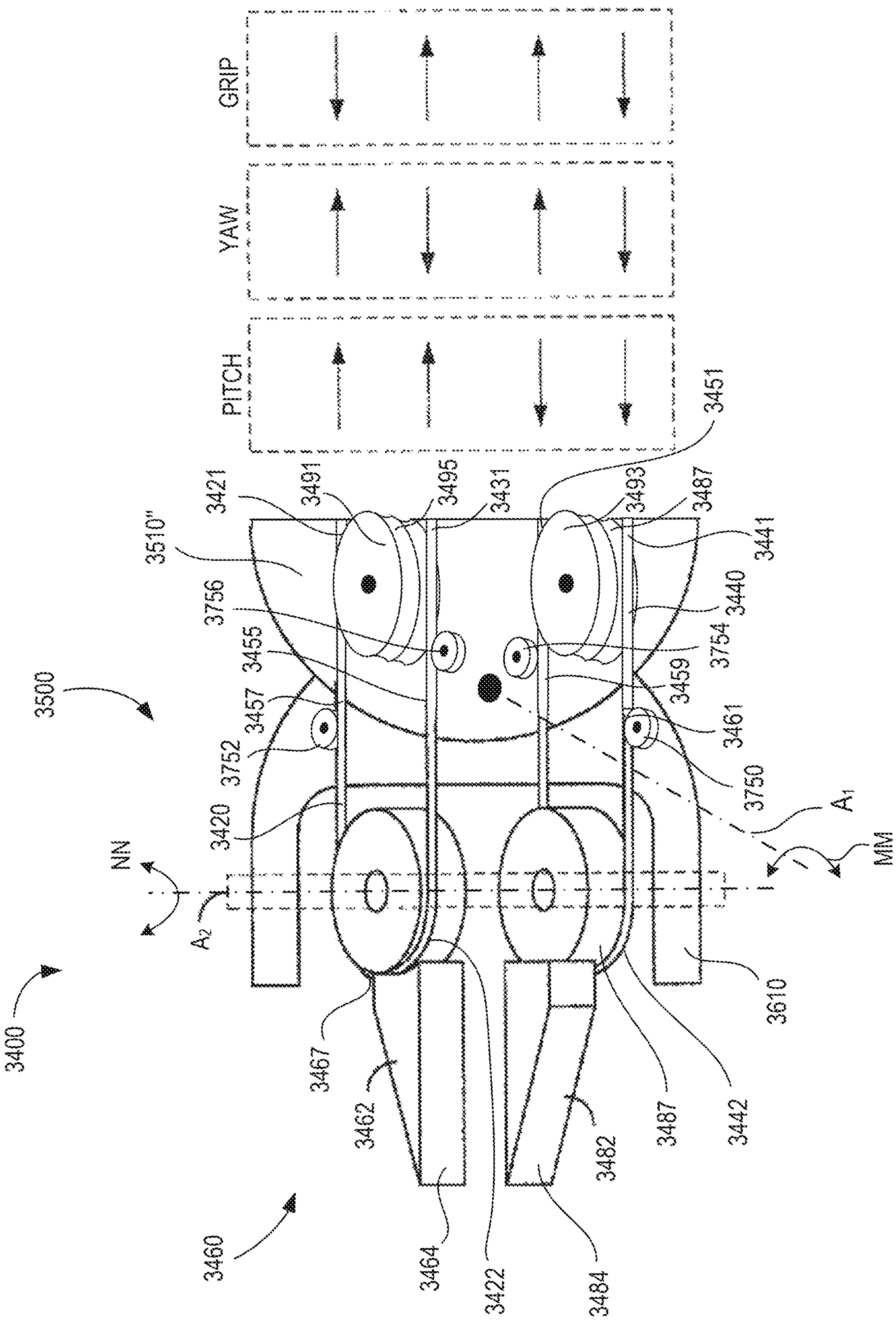

The pulleys 3491, 3493 can be any suitable pulley of the types shown and described herein, and can rotate relative to the first link 3510" along with the movement of the first, second, third and fourth end portions 3421, 3431, 3441 and 3451. The pulleys 3491, 3493 can have any suitable size. For example, in some embodiments, the first proximal guide pulley 3491 and the second proximal guide pulley 3493 can have a radius that is greater than a radius of the rollers. In some embodiments, the first proximal guide pulley 3491 and the second proximal guide pulley 3493 can have a radius that is at least twice a radius of the rollers. Moreover, although the embodiment shown in FIG. 8C shows the pulleys being included within the first link 3510", in other embodiments, the second link 3610 can also include any number of or arrangement of pulleys.

Figure 8D:
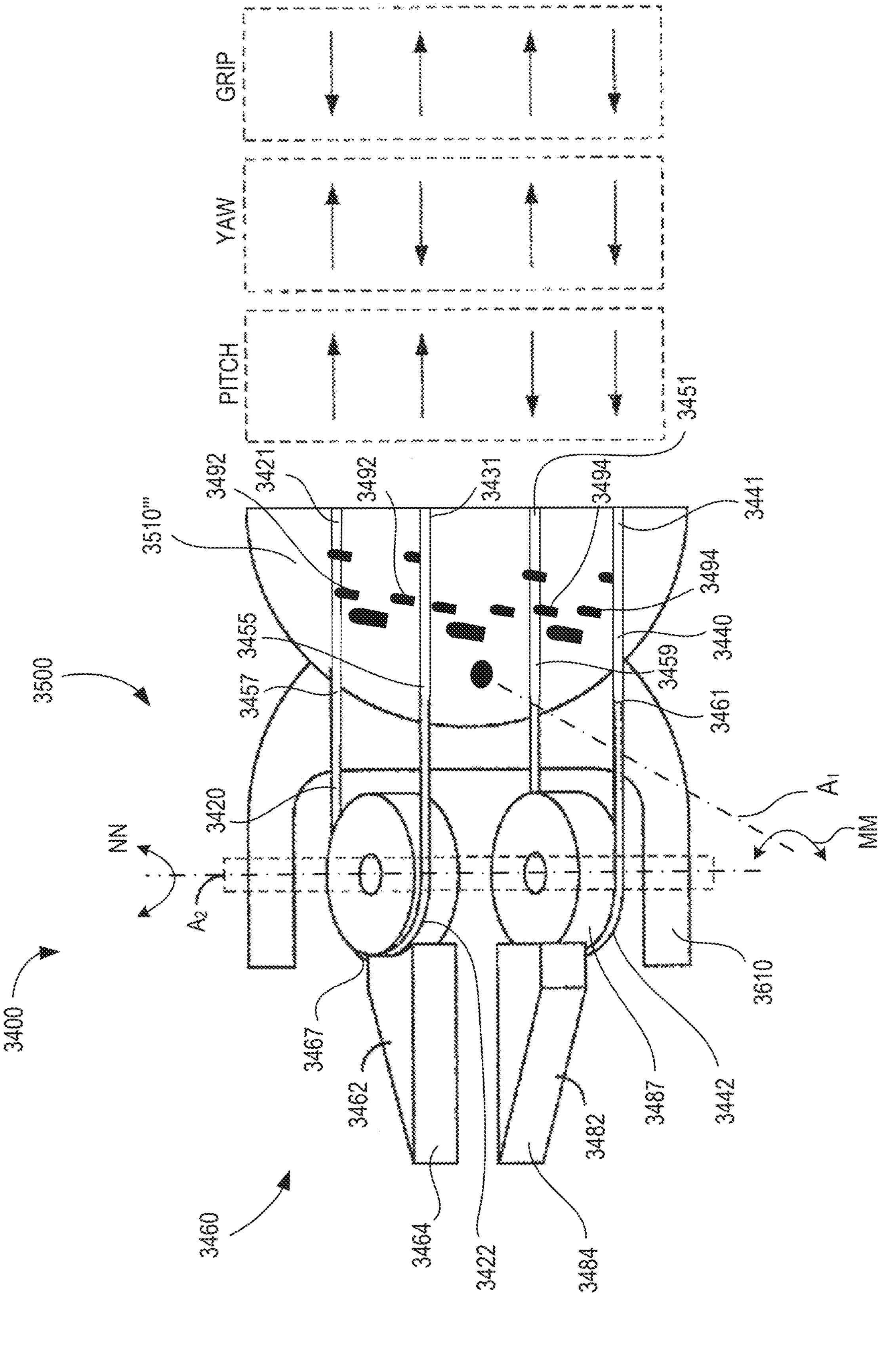
Figure 9:
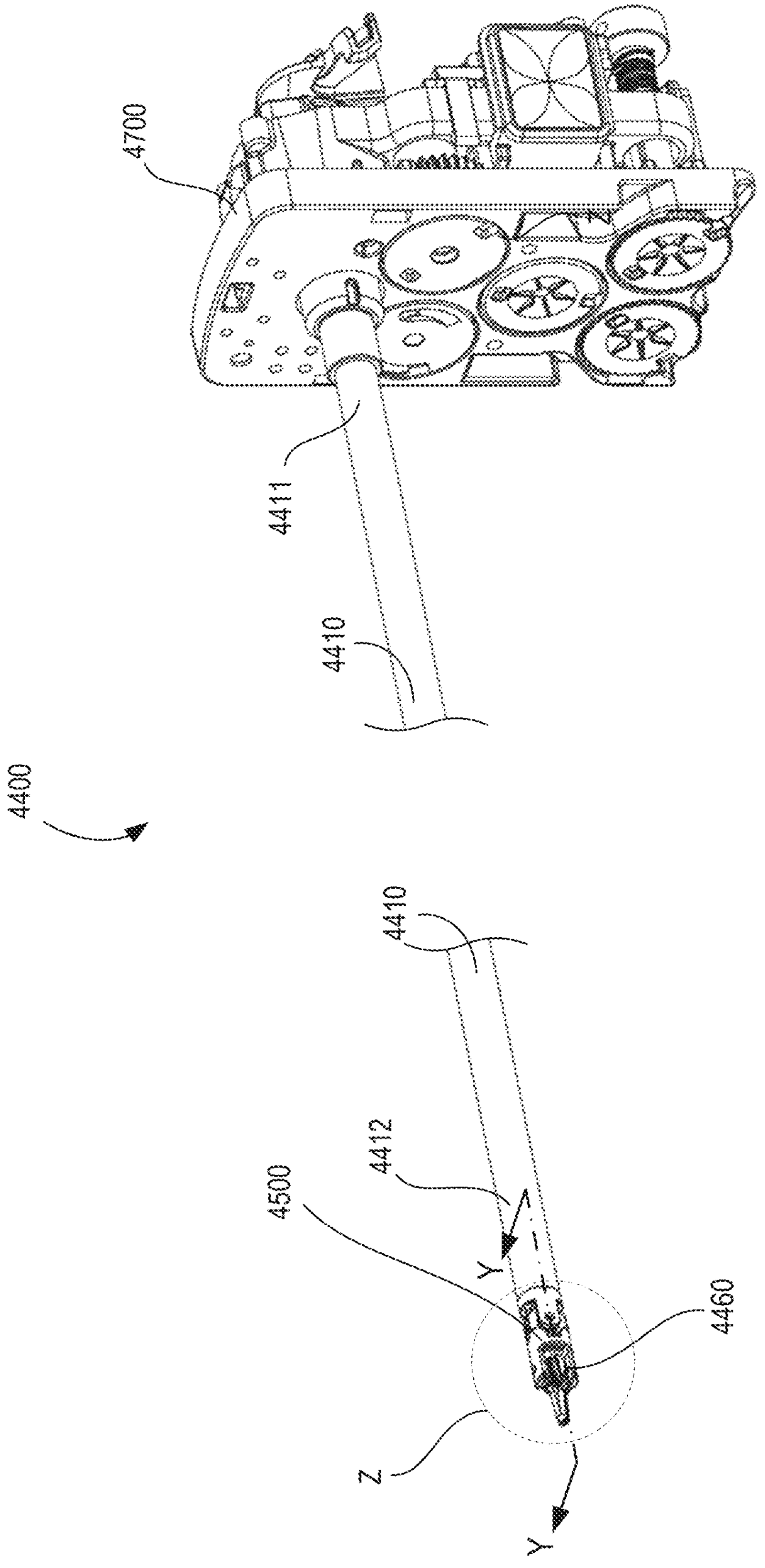
FIG. 9 is a perspective view of an instrument of a surgery system in a first orientation, according to an embodiment.

Any suitable structure can form any of the guide paths shown and described herein. For example, referring to FIG. 8D, in some embodiments, a first link 3410'" includes first proximal guide posts 3492 and a second proximal guide posts 3494, which can be included without the proximal rollers 3750, 3752 and distal rollers 3754, 3756. The first proximal guide posts 3492 are located between the first proximal end portion 3421 and the second proximal end portion 3431 of the first tension member 3420. The second proximal guide posts 3494 are located between the third proximal end portion 3441 and the fourth proximal end portion 3451 of the second tension member 3440. The first and second proximal guide posts 3492, 3494 are arranged to guide the first and second tension members 3420, 3440 during operation to ensure proper alignment for the first orientation shown in FIG. 8D and during pitch movements.

FIGS. 9-18 are various views of an instrument 4400, according to an embodiment. In some embodiments, the instrument 4400 or any of the components therein are optionally parts of a surgical assembly that performs minimally invasive surgical procedures, and which can include a patient-side cart, a series of kinematic linkages, a series of cannulas, or the like. The instrument 4400 (and any of the instruments described herein) can be used in any suitable surgical system, such as the MIRS system 1000 shown and described above. The instrument 4400 includes a transmission assembly 4700 (that can function as an actuator mechanism), an instrument shaft 4410, a wrist assembly 4500, and an end effector 4460.

Figure 10:
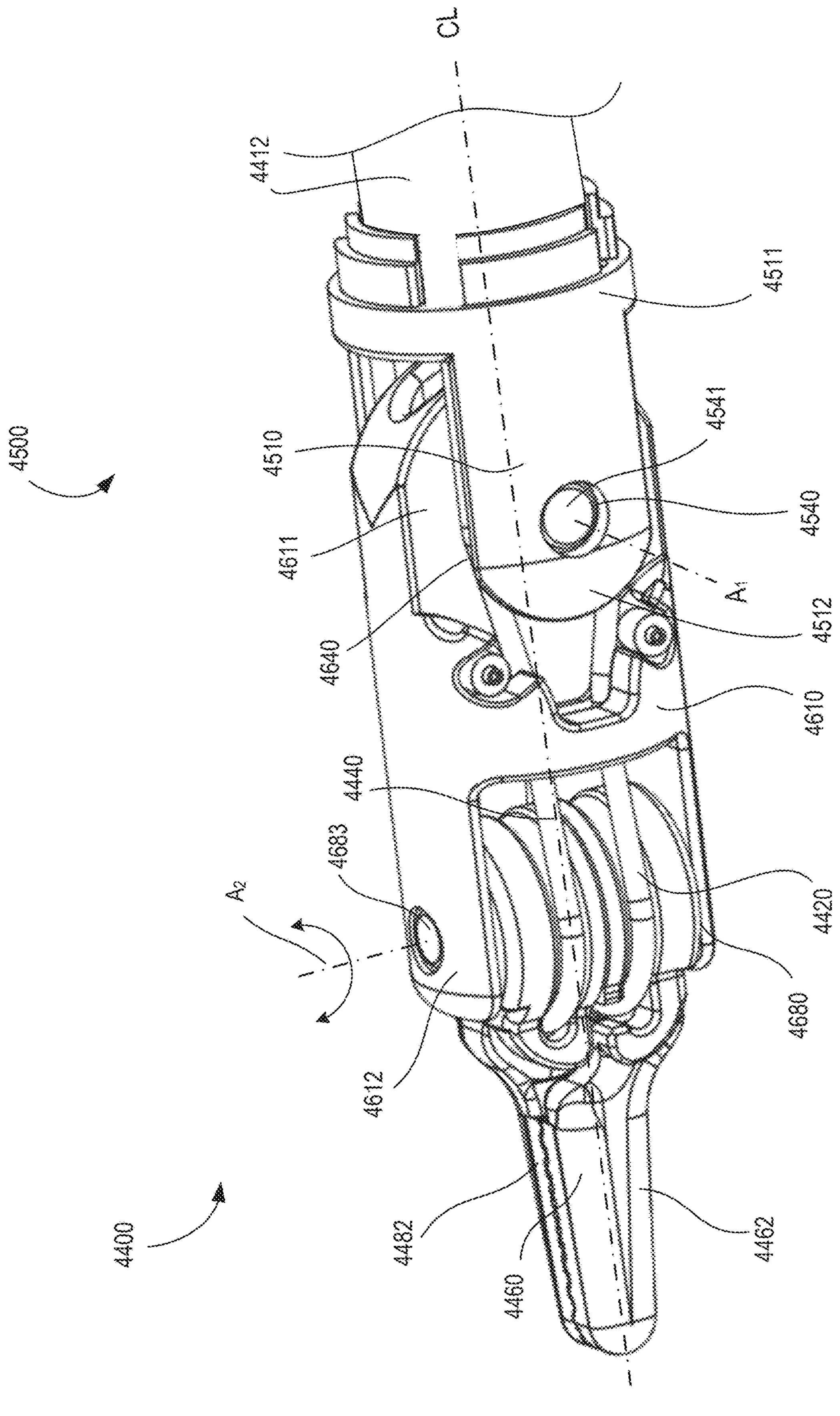
FIG. 10 is an enlarged perspective view of a distal end portion of the instrument indicated by the region Z shown in FIG. 9.

Referring to FIG. 10, the instrument 4400 also includes a first cable 4420 (which acts as a tension member) and a second cable 4440 (which acts as a tension member) that couple the transmission mechanism 4700 to the wrist assembly 4500. The instrument 4400 is configured such that movement of the cables can produce rotation of the wrist assembly 4500 (i.e., pitch rotation) about a first axis of rotation $A_1$, yaw rotation of the end effector 4460 about a second axis of rotation $A_2$, grip rotation of the tool members of the end effector 4460 about the yaw axis, or any combination of these movements. Changing the pitch, yaw, or grip of the instrument 4400 can be performed by manipulating the four cables in similar manner as that described above for the instrument 3400. Thus, the specific movement of each of the four cables to accomplish the desired motion is not described below. Although shown and described as including two cables that are wrapped about the end effector 4460 resulting in four proximal end cable portions (i.e., the four cable arrangement), in other embodiments, the instrument 4400 can include additional cables that separately change the pitch of the instrument 4400.

The transmission mechanism 4700 produces movement of each of the first cable 4420 and the second cable to produce the desired movement (pitch, yaw, or grip) at the wrist assembly 4500. Specifically, the transmission mechanism 4700 includes components and controls to move some of the cables in a proximal direction (i.e., to pull in certain cables) while simultaneously allowing the distal movement (i.e., releasing or "paying out") of other of the cables in equal lengths. In this manner, the backend mechanism 4700 can maintain the desired tension within the cables, and can ensure that the lengths of the cables are conserved (i.e., moved in equal amounts) during the entire range of motion of the wrist assembly 4500. In some embodiments, for example, the transmission assembly 4700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments, however, conservation of the lengths of the cables is not required.

In some embodiments, the transmission mechanism 4700 can include one or more linear actuators that produce translation (linear motion) of a portion of the cables. Such transmission mechanisms can include, for example, a gimbal, a lever, or any other suitable mechanism to directly pull (or release) an end portion of any of the cables. For example, in some embodiments, the transmission mechanism 4700 can include any of the transmission assemblies or components described in U.S. Patent Application Pub. No. US 2015/0047454 A1 (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety. In other embodiments, however, the transmission mechanism 4700 can include a capstan or other motor-driven roller that rotates or "winds" a portion of any of the cables to produce the desired cable movement. For example, in some embodiments, the backend mechanism 4700 can include any of the backend assemblies or components described in U.S. Pat. No. 9,204,923 B2 (filed Jul. 16, 2008), entitled "Medical Instrument Electronically Energized Using Drive Cables," which is incorporated herein by reference in its entirety.

The instrument shaft 4410 can be any suitable elongated shaft that couples the wrist assembly 4500 to the transmission mechanism 4700. Specifically, the instrument shaft 4410 includes a proximal end portion 4411 that is coupled to a housing of the backend mechanism 4700, and a distal end portion 4412 that is coupled to the wrist assembly 4500. The instrument shaft 4410 defines a passageway or series of passageways through which the cables and other components (e.g., electrical wires, ground wires, or the like) can be routed from the transmission mechanism 4700 to the wrist assembly 4500. Although shown as being cylindrical, in other embodiments, the instrument shaft 4410 can have any suitable shape.

Referring to FIG. 10-13, the wrist assembly 4500 includes a proximal first link 4510 and a distal second link 4610. The first link 4510 has a proximal end portion 4511 and a distal end portion 4512. The proximal end portion 4511 is coupled to the distal end portion 4412 of the instrument shaft 4410. The proximal end portion 4511 can be coupled to the instrument shaft 4410 via any suitable mechanism. For example, in some embodiments, the proximal end portion 4511 can be matingly disposed within a portion of the instrument shaft (e.g., via an interference fit). As shown, the proximal end portion 4511 can include one or more protrusions, recesses, openings, or connectors that couple the proximal end portion 4511 to the instrument shaft. The proximal end portion 4511 can be fixedly coupled to the instrument shaft 4410 via an adhesive bond, a weld, or any other permanent coupling mechanism (i.e., a coupling mechanism that is not intended to be removed during normal use).

The distal end portion 4512 includes a joint portion 4540 that is rotatably coupled to a mating joint portion 4640 of the second link 4610. In this manner, the first link 4510 and the second link 4610 form the wrist assembly 4500 having a first axis of rotation $A_1$ (also referred to as the pitch axis) about which the second link 4610 can rotate relative to the first link 4510. A pin 4541 extends through distal end joint portion 4540 and the second link joint portion 4640 to rotatably couple the second link 4610 to the first link 4510. As shown in FIG. 10, the first link 4510 and the second link 4610 define a longitudinal center line CL that intersects the pitch axis $A_1$ when the instrument is in an initial (or "straight" configuration).

Figure 12:
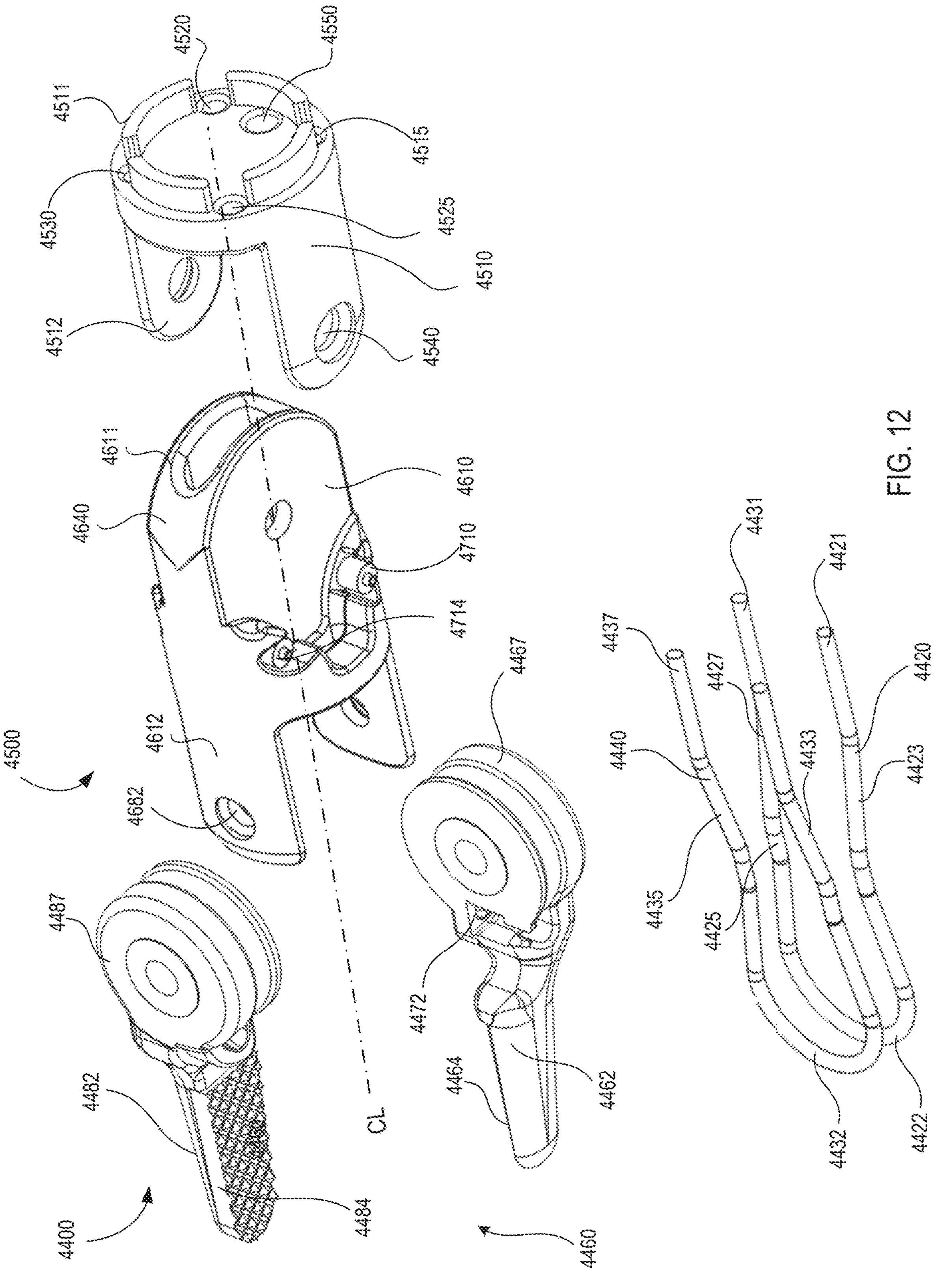
FIG. 12 is a perspective view of the distal end portion of the instrument of FIG. 10 shown in an exploded view.
Figure 13:
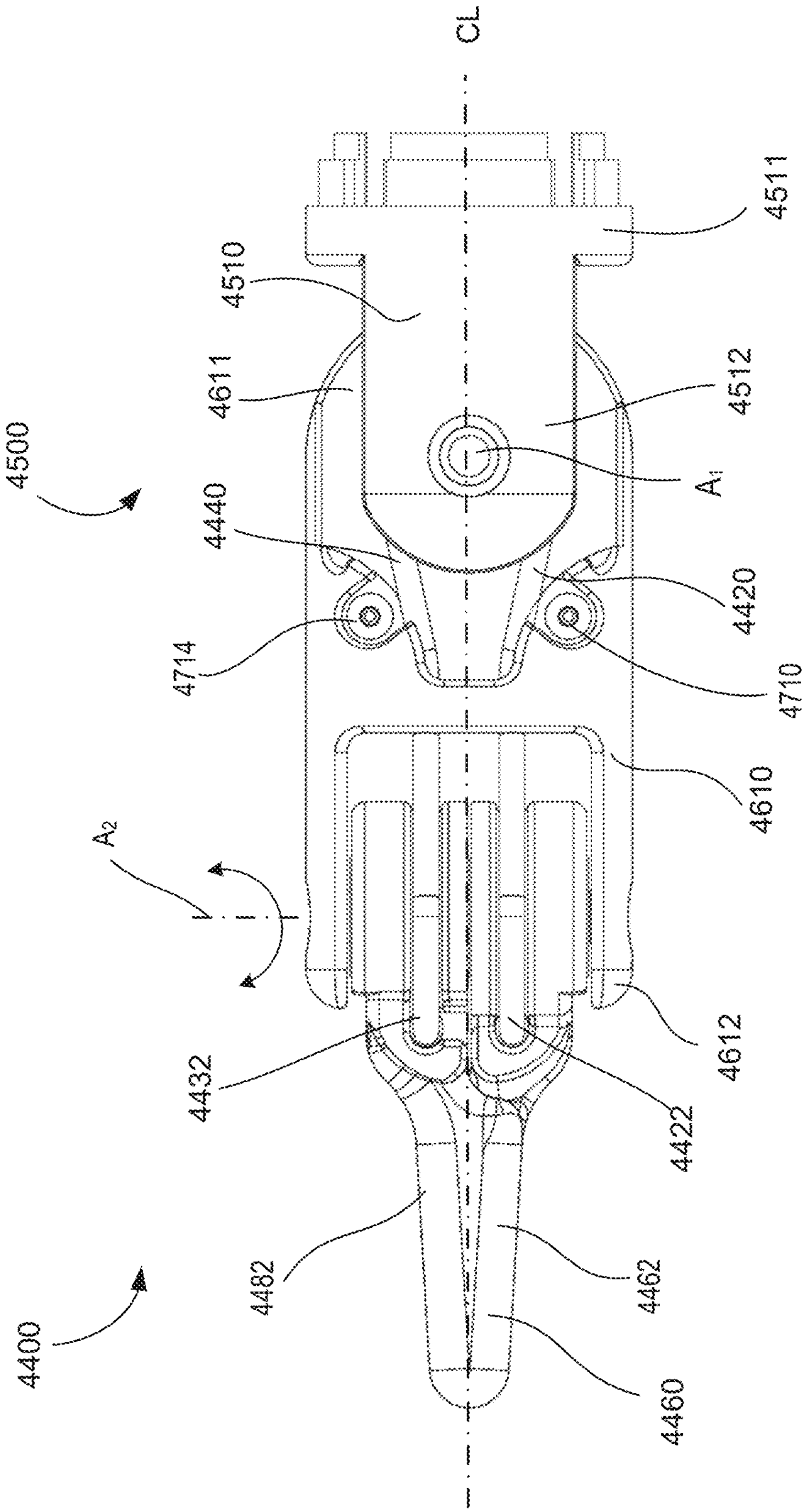
FIG. 13 is a side view of the distal end portion of the instrument of FIG. 10 in a first orientation taken along line Y-Y shown in FIG. 9.
Figure 14:
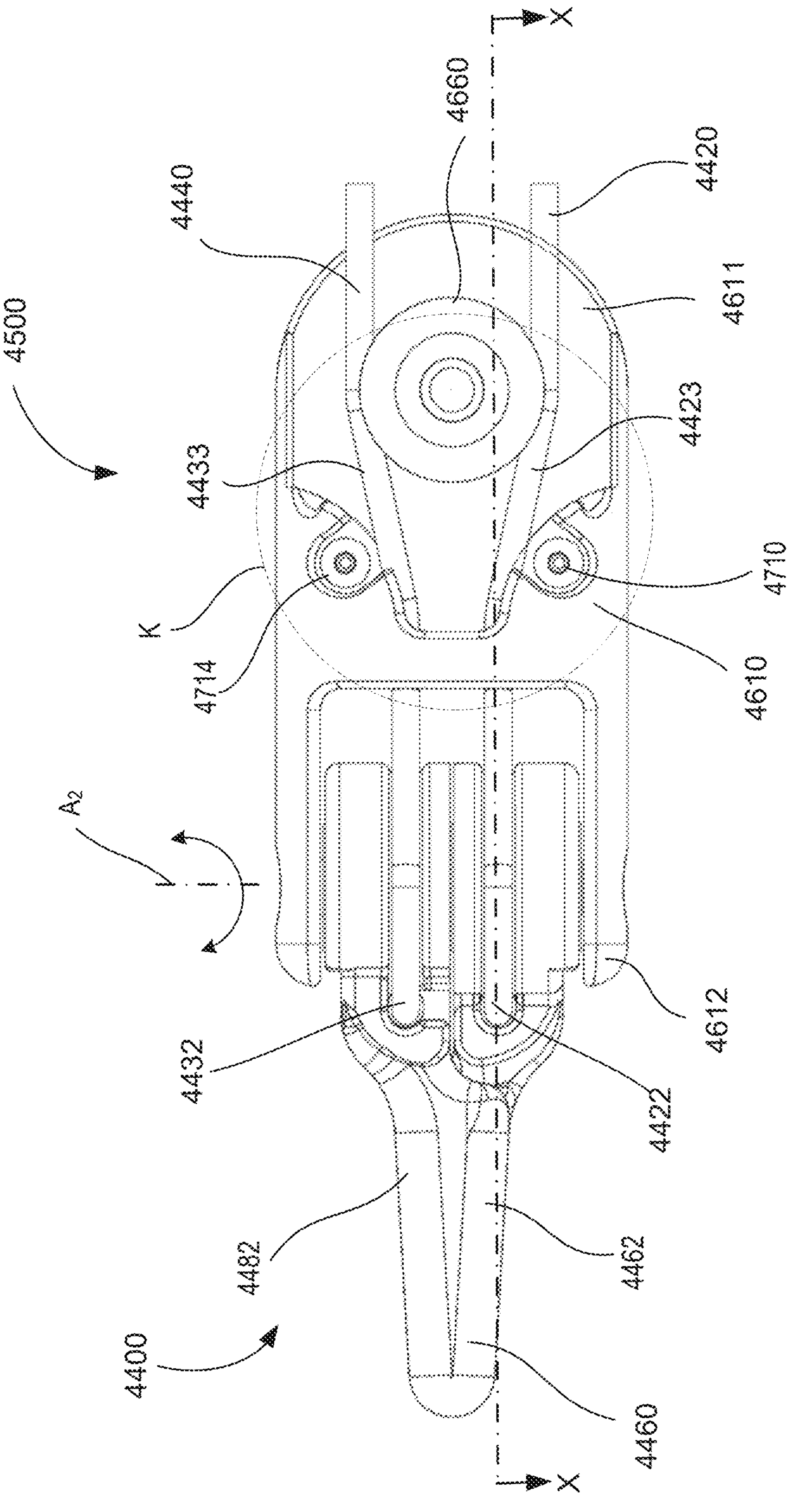
FIG. 14 is a side view of the distal end portion of the instrument of FIG. 13 in a first orientation shown with the first link removed to expose portions of the cables.
Figure 15:
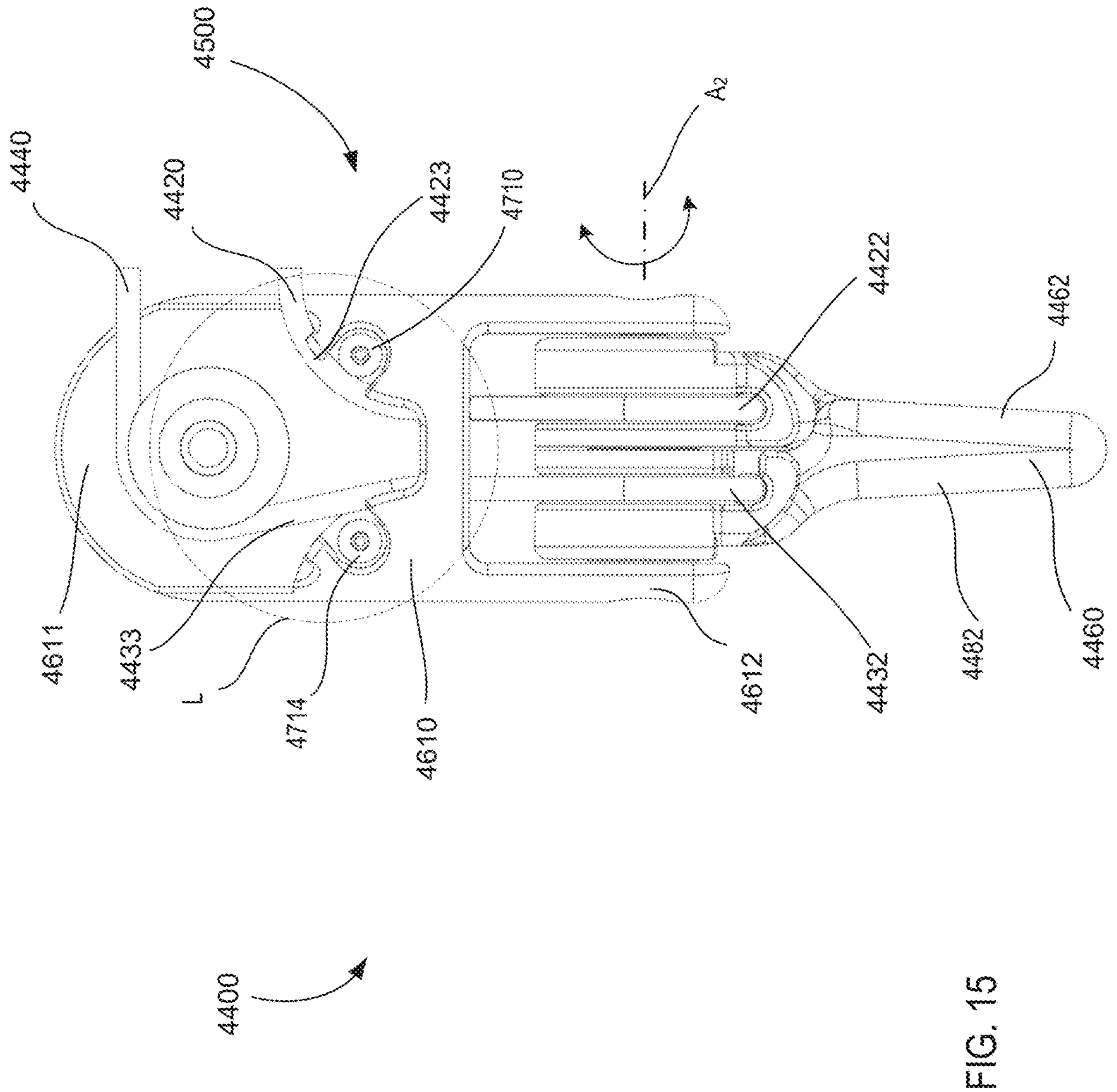
FIG. 15 is a side view of the distal end portion of the instrument of FIG. 13 in a second orientation shown with the first link removed to expose portions of the cables.
Figure 16:
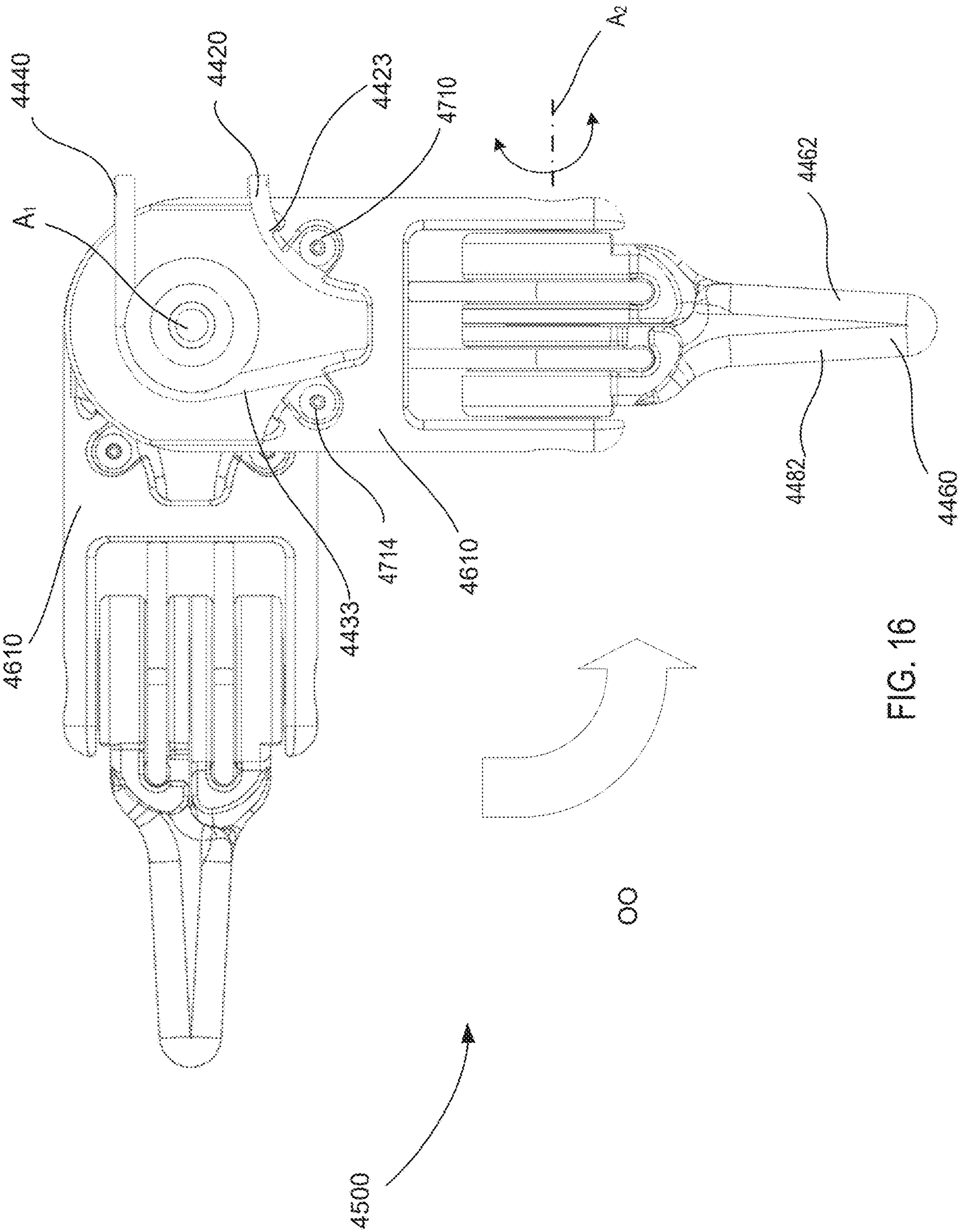
FIG. 16 is a side view of the distal end portion of the instrument of FIG. 13 showing the second orientation of FIG. 15 superimposed over the first orientation of FIG. 14, and both shown with the first link removed to expose portions of the cables.

Referring to FIG. 12, a first guide channel 4515, a second guide channel 4520, a third guide channel 4525, and a fourth guide channel 4535 are defined in the first link 4510. A first proximal end portion 4421 of the first cable 4420 is movably disposed within the first guide channel 4515. A second proximal end portion 4431 of the first cable 4420 is movably disposed within the second guide channel 4520. In this manner, the portions of the first cable 4420 coupled to the first tool member 4462 are within guide channels that are separated. In some embodiments, however, the first guide channel 4515 can be combined with the second guide channel 4520 to form a single channel within which the first proximal end portion 4421 and the second proximal end portion 4431 are disposed. A first proximal end portion 4441 of the second cable 4440 is movably disposed within the third guide channel 4525. A second proximal end portion 4451 of the second cable 4440 is movably disposed within the fourth guide channel 4530. In some embodiments, the third guide channel 4525 can be combined with the fourth guide channel 4530 to form a single channel within which the first proximal end portion 4441 and the second proximal end portion 4451 are disposed.

The first link 4510 also defines additional bores or guide channels 4550. The additional guide channels 4550 can contain (or allow passage of) various components of the wrist assembly, such as, for example, electrical wires. In some embodiments, the guide channels 4550 can contain additional cables (not shown) that are coupled to the second link 4610 and that cause the second link 4610 to rotate relative to the first link 4510 (i.e., a pitch rotation) when the cables are moved. In this manner, the wrist assembly 4500 can be a six-cable configuration (two cables or portions of cables controlling the pitch rotation and four cables or portions of cables controlling the yaw and grip rotations).

The distal second link 4610 has a proximal end portion 4611 and a distal end portion 4612. As described above, the proximal end portion 4611 includes a joint portion 4640 that is rotatably coupled to the joint portion 4540 of the first link 4510. The distal end portion 4612 of the second link 4610 includes a connector 4680 that is coupled to the end effector 4460. In this manner, the first tool member 4462 and the second tool member 4482 can rotate relative to the second link 4610 about a second axis of rotation (also referred to as the yaw axis) $A_2$. The connector 4680 is a pin-type connector and includes the pin 4683 which is supported by (and placed within) the pin openings 4682. In some embodiments, the connector 4680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 10, the second axis of rotation $A_2$ (also referred to as the yaw axis) is non-parallel to the pitch axis $A_1$. Thus, the instrument 4400 provides for up to three degrees of freedom (i.e., a pitch motion about the first axis of rotation $A_1$, a yaw rotation about the second axis of rotation $A_2$, and a grip motion about the second axis of rotation $A_2$).

Figure 11:
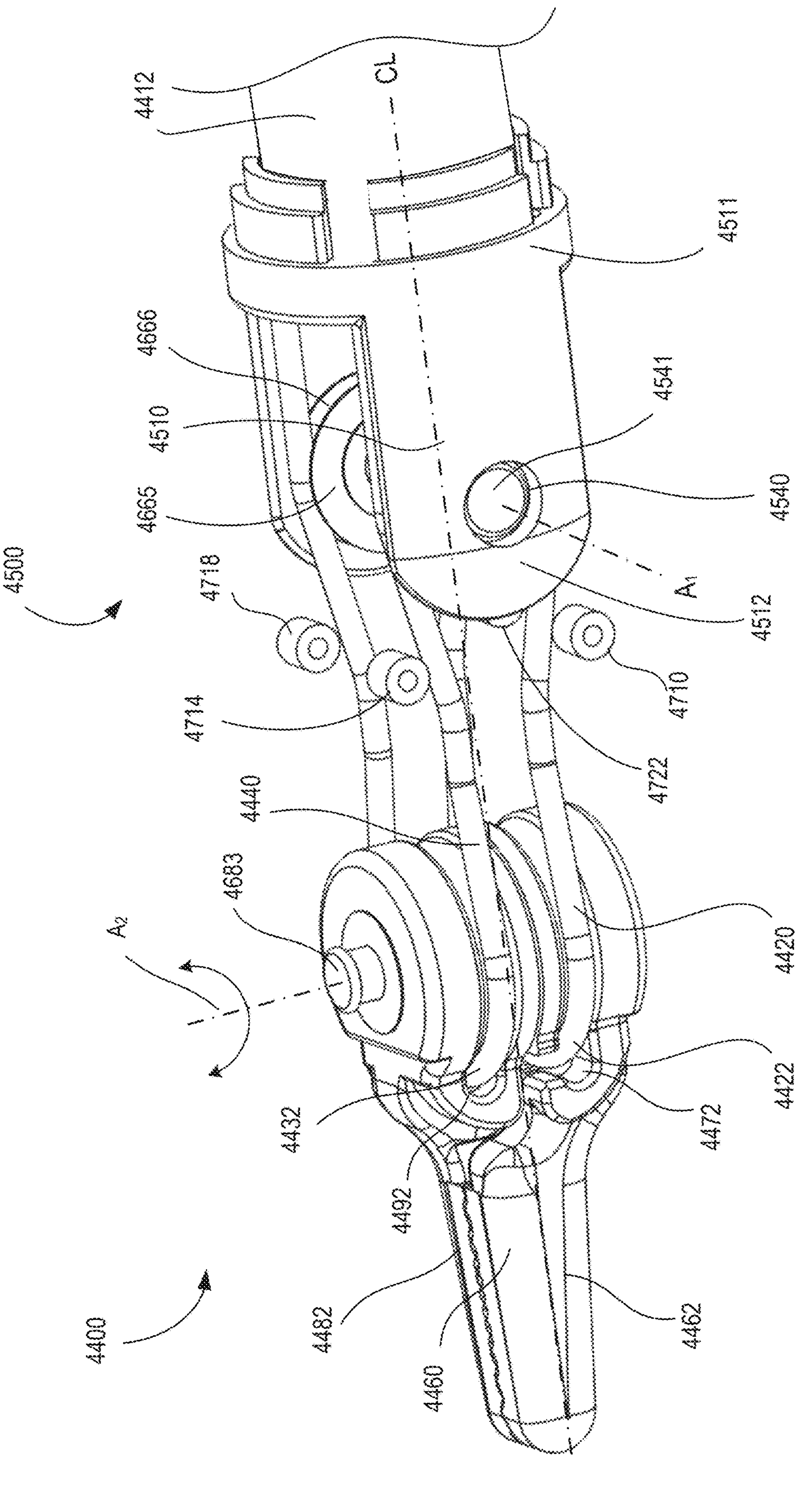
FIG. 11 is a perspective view of the distal end portion of the instrument of FIG. 10 shown with the second link removed to expose portions of the cables.
Figure 17:
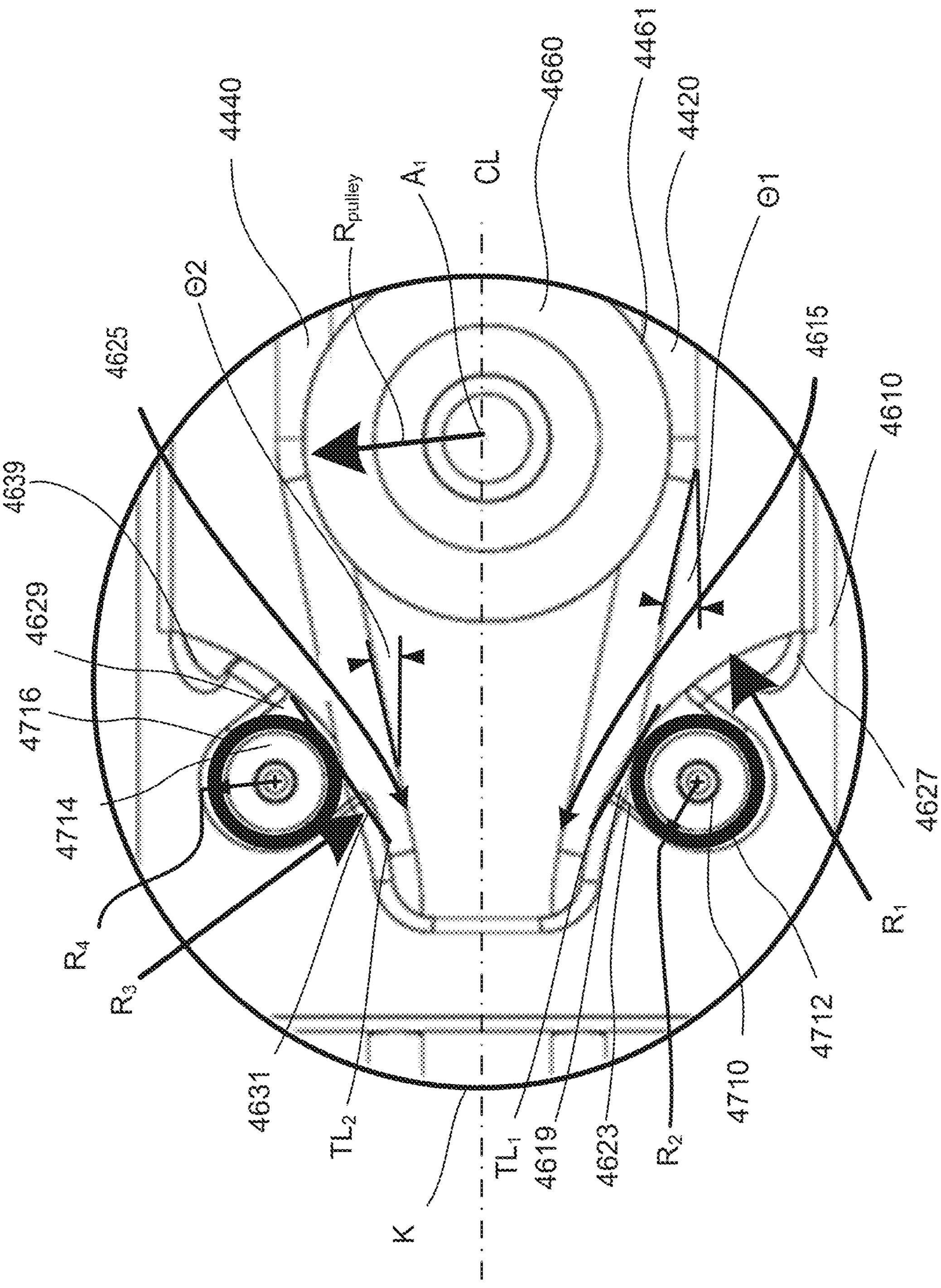
FIG. 17 is an enlarged side view of a distal end portion of the instrument of FIG. 14 in the first orientation indicated by the region K shown in FIG. 14.
Figure 18:
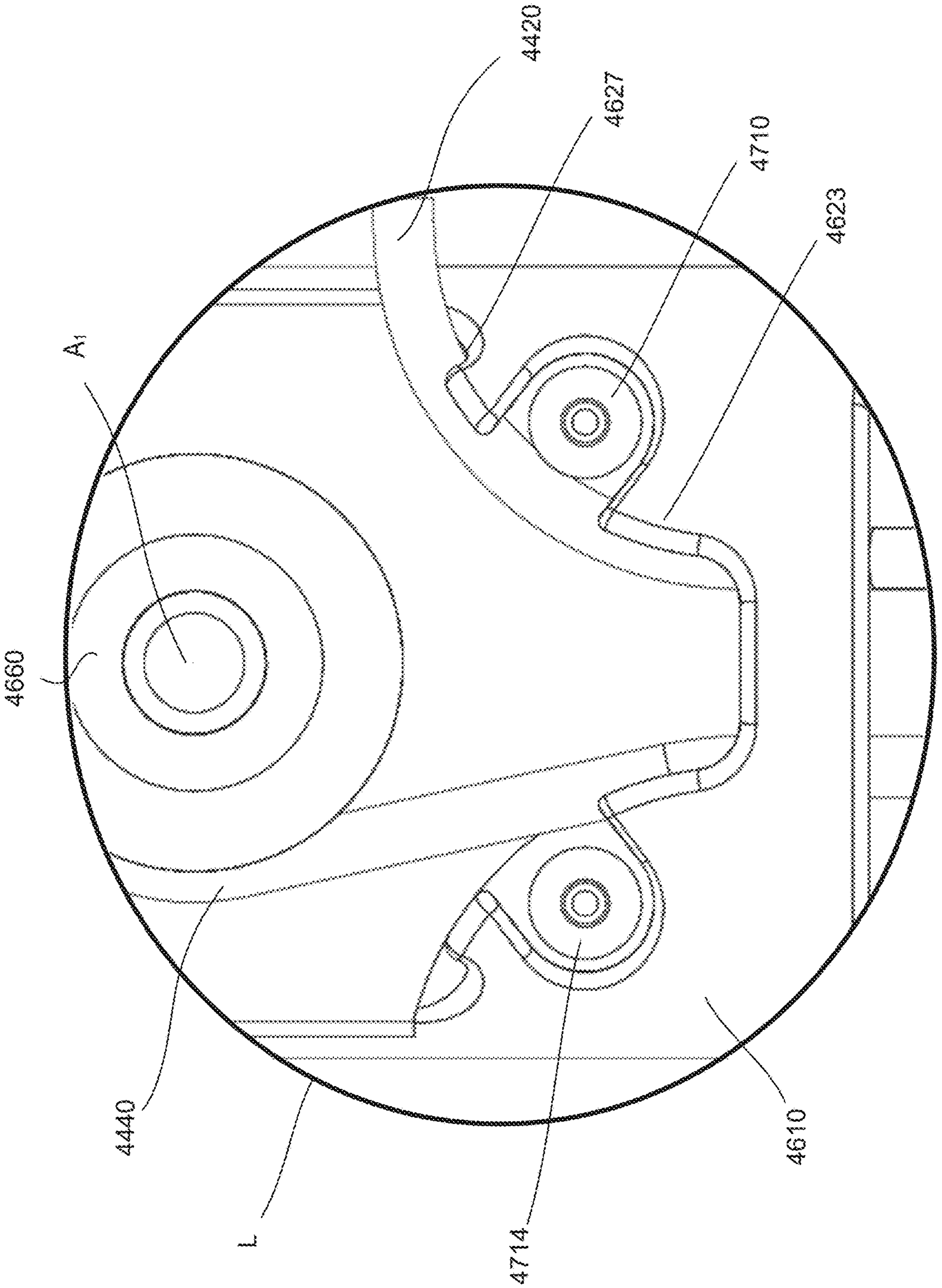
FIG. 18 is an enlarged side view of a distal end portion of the instrument of FIG. 15 in the second orientation indicated by the region L shown in FIG. 15.

Referring to FIGS. 11 and 12, the second link 4610 includes a first pulley 4660 (see also FIGS. 14 and 17), a second pulley 4665, a first roller 4710, a second roller 4714, a third roller 4718, and a fourth roller 4722. The first pulley 4660 and the second pulley 4665 are each rotatably coupled to the second link 4610 via the pin 4541. In this manner, the first pulley 4660 and the second pulley 4665 can each rotate relative to the second link 4610 about the first axis of rotation $A_1$. The first pulley 4660 includes an outer surface 4661 within a grooved channel (see FIG. 17), and the second pulley 4665 includes an outer surface 4666 within a grooved channel (see FIG. 11). This arrangement allows the first central portion 4423 of the first cable 4420 and third central portion 4433 of the second cable 4440 to each contact the outer surface 4661 of the first pulley (see FIGS. 14 and 17), depending on the orientation of the wrist assembly 4500. Although not shown, the second central portion 4425 of the first cable 4420 and the fourth central portion 4435 of the second cable 4440 can similarly contact the outer surface 4666 of the second pulley 4665. Thus, this arrangement provides one pulley that functions to engage and define a portion of a guide path for two distinct cable portions. As shown in FIG. 17, the radius of the first pulley 4660 and the second pulley 4665 is identified as $R_{pulley}$, and is selected to produce the desired guide path and fleet angle, as described below.

The first roller 4710, the second roller 4714, the third roller 4718, and the fourth roller 4722 are each rotatably coupled to the second link 4610 via a pin. Specifically, each of the rollers are coupled within a pocket defined by the second link 4610. For example, referring to FIG. 17, the first roller 4710 is coupled within a first pocket 4619 and the second roller 4714 is coupled within a second pocket 4629. Each of the rollers includes an outer surface that can contact a portion of a cable. Specifically, the first roller 4710 includes a first outer surface 4712 and the second roller 4714 includes a second outer surface 4716. As described in more detail below, the rollers can rotate along with the movement of the cables to reduce friction of the cables, especially when the when the instrument 4400 is at a high pitch orientation. The rollers can be any suitable rollers, and can have any suitable size. For example, in some embodiments, the rollers can include a bearing surface that rotates against its mounting pin. In other embodiments, the rollers can include separate bearings (ball bearing, roller bearings, or the like) that reduce the friction when the rollers rotate relative to the second link 4610. The rollers can be any suitable size that limits the maximum amount of bend (i.e., that prevents the cables from bending too sharply) when the cables are wrapped about or in contact with the rollers. As shown in FIG. 17, the first roller 4710 has a radius $R_2$ and the second roller 4714 has a radius $R_4$. In some embodiments, the radius $R_2$ and the radius $R_4$ can be the same (i.e., the first roller 4710 and the second roller 4714 are the same size). In some embodiments, the rollers have a smaller radius than that of the first pulley 4660 or the second pulley 4665 (i.e., the radius $R_2$ can be less than the radius $R_{pulley}$). For example, in some embodiments, the radius $R_2$ is less than half the radius $R_{pulley}$.

As shown in FIG. 17, the second link 4610 defines a first curved guide path 4615 and a second curved guide path 4625. The second link 4610 also includes a first guide surface 4623 and a second guide surface 4627 that are aligned with a portion of the first curved guide path 4615. Moreover, the first roller 4710 is rotatably coupled to the second link 4610 (within the first pocket 4619 that separates the first guide surface 4623 from the second guide surface 4627) such that the first outer surface 4712 is aligned with the first curved guide path 4615 along with the first guide surface 4623 and the second guide surface 4627. Similarly stated, the first roller 4710 is positioned such that a first tangent line $TL_1$ to the first roller surface 4712 is tangent to the first curved guide path 4615. The second link 4610 also includes a third guide surface 4631 and a fourth guide surface 4639 that are aligned with a portion of the second curved guide path 4625. The second roller 4714 is rotatably coupled to the second link 4610 (within the second pocket 4629 that separates the third guide surface 4631 from the fourth guide surface 4639) such that the second outer surface 4716 is aligned with the second curved guide path 4625 along with the third guide surface 4631 and the fourth guide surface 4639. Similarly stated, the second roller 4714 is positioned such that a second tangent line $TL_2$ to the second roller surface 4716 is tangent to the second curved guide path 4625.

The first and second curved guide paths 4615, 4625 (and therefore the portions of the first cable 4420 and the second cable 4440 therein) are each offset from the longitudinal center line CL and the first axis of rotation $A_1$. In this manner, application of a force via the first cable 4420 or the second cable 4440 produces a torque about the first axis of rotation $A_1$. This can result in rotation of the second link 4610 relative to the first link 4510 (i.e., pitch), as shown by the arrow OO in FIG. 16 for application of a force via the first cable 4420. The amount of cable offset from the longitudinal center line CL is also based in part on the size of the pulley 4660. As shown in FIG. 17, the outer surface 4661 of the pulley 4660 contacts the first central portion 4423 of the first cable 4420 and the third central portion 4433 of the second cable 4440 when the instrument 4400 is in certain orientations. Thus, the radius $R_{pulley}$ of the pulley 4660 defines the amount of offset. The radius $R_{pulley}$ of the pulley 4660 also defines a fleet angle Θ1 (see FIG. 17) between the pulley 4660 and the pulley portion 4467 of the first tool member 4462 and a fleet angle Θ2 between the pulley 4660 and the pulley portion 4487 of the second tool member 4482. In some embodiments, the fleet angle Θ1 and the fleet angle Θ2 can be less than about 10 degrees. In other embodiments, the fleet angle Θ1 and the fleet angle Θ2 can be between about 5 degrees and 10 degrees. In yet other embodiments, the fleet angle Θ1 and the fleet angle Θ2 can be between about 5 degrees and 15 degrees.

Figure 19:
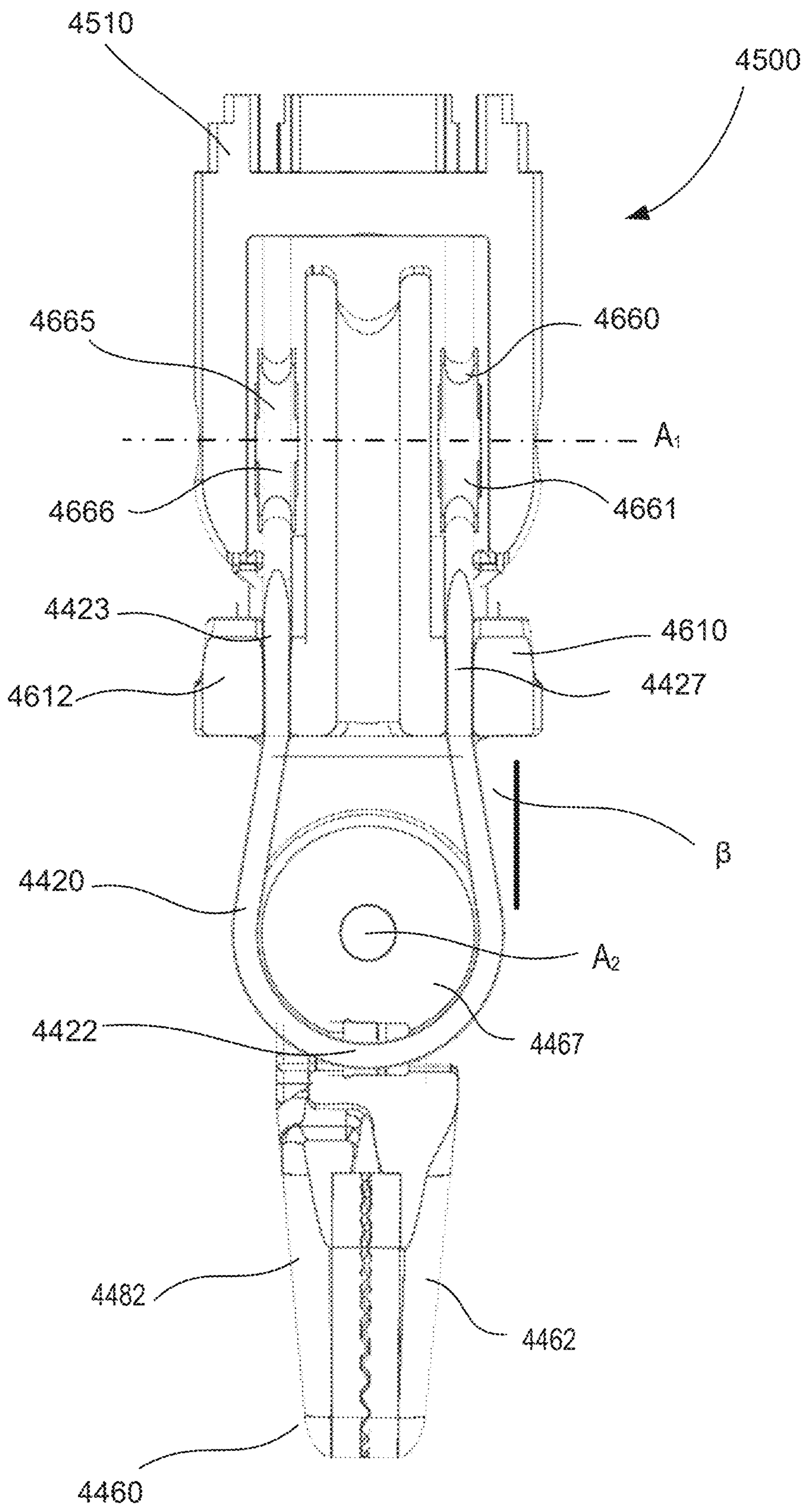
FIG. 19 is a cross-sectional view of the distal end portion of the instrument of FIG. 10 in a first orientation taken along line X-X shown in FIG. 14.

In addition to defining the fleet angles Θ1, Θ2 within a plane normal to the first axis of rotation $A_1$ as shown in FIG. 17, the distance between the pulley 4660 and the pulley 4665 along the first axis of rotation $A_1$ also defines a fleet angle β in a plane normal to the second axis of rotation $A_2$. Referring to FIG. 19, the fleet angle β is defined along the first cable 4420 between the pulley 4660 (and the guide surface 4623) and the pulley portion 4467 of the first tool member 4462. Decreasing the distance between the pulley 4660 and the pulley 4465 is desirable to allow for a reduced size shaft or wrist assembly 4500, but also results in an increased fleet angle β. Increasing the size of the pulley portion 4467 increases the moment arm of the first cable 4420 about the first tool member 4462, which can be desirable. Increasing the size of the pulley portion 4467 also results in an increased fleet angle β. In some embodiments, the fleet angle β and the fleet angle β can be less than about 10 degrees. In other embodiments, the fleet angle β and the fleet angle β can be between about 5 degrees and 10 degrees. In yet other embodiments, the fleet angle β can be between about 5 degrees and 15 degrees.

As shown in FIG. 12, the end effector 4460 includes a first tool member 4462 and a second tool member 4482. The first tool member 4462 includes a contact portion 4464 and a pulley portion 4467. The contact portion 4463 is configured engage or manipulate a target tissue during a surgical procedure. Although shown as being a gripping surface, in other embodiments, the contact portion 4464 can be any suitable surface of the types shown and described herein (e.g., a cutter, a tissue manipulator, a cauterizing surface, or the like). As shown in FIGS. 10 and 11, the pulley portion 4467 is rotatably coupled to the second link 4610 via the pin 4683. In this manner, the first tool member 4462 can rotate about the pin 4683 and relative to the second link 4610 via the second axis of rotation $A_2$. Moreover, the pulley portion 4467 defines the coupling openings 4472 within which the distal end portion 4422 of the first cable 4420 is coupled. The outer surface of the pulley portion 4467 is offset from the yaw axis $A_2$. In this manner, application of a force by the first cable 4420 on the pulley portion 4467 produces a torque on the first tool member 4462 about the yaw axis $A_2$, which can result in rotation of the first tool member 4462 or the application of a gripping force.

As shown in FIG. 12, the second tool member 4482 includes a contact portion 4484 and a pulley portion 4487. The contact portion 4484 is configured engage or manipulate a target tissue during a surgical procedure. Although shown as being a gripping surface, in other embodiments, the contact portion 4484 can be any suitable surface of the types shown and described herein (e.g., a cutter, a tissue manipulator, a cauterizing surface, or the like). As shown in FIGS. 10 and 11, the pulley portion 4487 is rotatably coupled to the second link 4610 via the pin 4683. In this manner, the second tool member 4482 can rotate about the pin 4683 and relative to the second link 4610 via the second axis of rotation $A_2$. As shown in FIG. 11, the pulley portion 4487 defines the coupling openings 4492 within which the distal end portion 4432 of the second cable 4440 is coupled. The outer surface of the pulley portion 4487 is offset from the yaw axis $A_2$. In this manner, application of a force by the second cable 4440 on the pulley portion 4487 produces a torque on the second tool member 4482 about the yaw axis $A_2$, which can result in rotation of the second tool member 4482 or the application of a gripping force.

As shown in FIG. 12, the first cable 4420 has a first proximal end portion 4421, a first central portion 4423, a distal end portion 4422, a second central portion 4425, and a second proximal end portion 4427. The second cable 4440 has a third proximal end portion 4431, a third central portion 4433, a distal end portion 4432, a fourth central portion 4435, and a fourth proximal end portion 4437. The proximal end portions 4421, 4427, 4431, 4437 each extend outside of the wrist assembly 4500, through the instrument shaft 4410, and into the transmission mechanism 4700. As described above, the transmission mechanism 4700 can move the proximal end portions 4421, 4427, 4431, 4437 to produce a resulting movement (or force) at the respective distal end portions 4422, 4432 of the cables. The first central portion 4423 of the first cable 4420 and the third central portion 4433 of the second cable 4440 are within the curved guide paths 4615, 4625, as described above along with FIG. 17. The shape of the first and second curved guide paths 4615, 4625 are such that the first cable 4420 and the second cable 4440 are routed through the wrist assembly 4500 in a manner that maintains the desired bend geometry, cable tension, and the like during actuation of the instrument 4400. Similarly, the second central portion 4425 of the first cable 4420 and the fourth central portion 4425 of the second cable 4440 are within corresponding third and fourth curved guide paths (not shown), as described above for the first and second curved guide paths 4615, 4625. The shape of the third and fourth curved guide paths (not shown) are such that the first cable 4420 and the second cable 4440 are routed through the wrist assembly 4500 in a manner that maintains the desired bend geometry, cable tension, and the like during actuation of the instrument 4400. As described above, the distal end portion 4422 is coupled to the first tool member 4462 and the distal end portion 4433 is coupled to the second tool member 4482 via a pin or swage coupling (i.e., within the coupling openings 4472, 4492). In this manner, as described herein, movement of (or a force applied to) the cables can produce pitch, yaw, grip or any combination of these motions.

The cables 4420 and 4430 can have any suitable shape. The use of the cables can provide for a low-cost, disposable instrument that is suitable for minimally-invasive surgical procedures. In use, the distal end portion of the instrument 4400 provides for up to three degrees of freedom, and can be moved between multiple different configurations to perform a variety of surgical operations.

In use, the wrist assembly 4500 can be moved between various orientations. As shown by the arrow OO in FIG. 16, the wrist assembly 4500 can be moved between a first (or straight) orientation and a second orientation by rotating the second link 4610 relative to the first link 4510 about the first axis of rotation $A_1$. Similarly, the second link 4610 can be rotated in an opposite direction about the first axis of rotation $A_1$ to a third orientation (not shown). When the wrist assembly 4500 is in the first orientation, the first cable 4420 is within the first cable path 4615 and the second cable 4440 is within the second cable path 4625. More particularly, the first central portion 4423 is in contact with the first guide surface 4623 of the second link 4610 and the surface 4661 of the pulley 4660. The third central portion 4433 is in contact with the third guide surface 4631 of the second link 4610 and the surface 4661 of the pulley 4660. When the first cable 4420 and the third cable 4440 are moved in the same direction (e.g., to produce a yaw motion of the end effector 4460), one of the first central portion 4423 or the third central portion 4433 will move along with rotation of the pulley 4660, and the other of the first central portion 4423 or the third central portion 4433 will slide against the surface 4461. Typically, the cable that has the greater wrap angle about the pulley 4660 (i.e., the cable that has the greater amount of friction with the surface 4461) will cause the pulley 4660 to rotate, and the cable with the lesser wrap angle (i.e., the cable that has the lower amount of friction) will slide against the surface 4461. In this manner, the pulley 4660 advantageously reduces the friction at the area of highest friction. This arrangement allows for efficient operation of the end effector 4460 regardless of the pitch orientation of the wrist assembly 4500.

When the wrist assembly 4500 is in the second orientation (FIGS. 15 and 16), the first central portion 4423 of the first cable 4420 remains within the first cable path 4615 and is in contact with the first guide surface 4623, the second guide surface 4627 and the roller surface 4712. Moreover, the first central portion 4423 is spaced apart from the pulley 4660. When axial tension is applied to the first cable 4420 for pitch movements or movement of the tool member 4462 for yaw or grip movements, the roller 4710 rotates along with movement of the first central portion 4423. The rotation of the roller 4710 is based on contact with the cable 4420 at the roller surface 4712, and reduces friction that would otherwise occur when the cable slides against the surfaces of the second link 4610 when tension is applied for pitch, yaw, or grip movements. Further, the roller 4710 advantageously reduces friction at a position along the curved guide path 4615 proximate to the first guide surface 4623 where high tensile stress is applied when the cable is tightly retained within the curved guide path about the bend radius $R_1$. In some embodiments, the radius of curvature $R_1$ of the first and second guide surface 4623, 4627 is larger than the radius $R_2$ of the roller 4710. In some embodiments, the radius of curvature $R_1$ is at least twice as large as the radius $R_2$.

When the wrist assembly 4500 is in the second orientation (FIGS. 15 and 16), the third central portion 4433 of the second cable 4440 remains within the second cable path 4625, but is spaced apart from the third guide surface 4631, the fourth guide surface 4639 and the roller surface 4716. Instead, the third central portion 4433 is in contact with (and at least partially wrapped about) the surface 4661 of the pulley 4660. Thus, when axial tension is applied to the second cable 4440 for pitch movements or movement of the second tool member 4482 for yaw or grip movements, the pulley 4660 rotates along with movement of the third central portion 4433. The rotation of the pulley 4660 is based on contact with the second cable 4440 at the pulley surface 4661, and reduces friction that would otherwise occur when the cable slides against the surfaces of the second link 4610 when tension is applied for pitch, yaw, or grip movements.

When the wrist assembly 4500 is in the third orientation (not shown), the first central portion 4423 of the first cable 4420 remains within the first cable path 4615, but is spaced apart from the first guide surface 4623, the second guide surface 4627 and the roller surface 4712. Instead, the first central portion 4423 is in contact with (and at least partially wrapped about) the surface 4661 of the pulley 4660. Thus, when axial tension is applied to the first cable 4420 for pitch movements or movement of the first tool member 4462 for yaw or grip movements, the pulley 4660 rotates along with movement of the first central portion 4423. The rotation of the pulley 4660 is based on contact with the first cable 4420 at the pulley surface 4661, and reduces friction that would otherwise occur when the cable slides against the surfaces of the second link 4610 when tension is applied for pitch, yaw, or grip movements.

When the wrist assembly 4500 is in the third orientation (not shown), the third central portion 4433 of the second cable 4440 remains within the second cable path 4625, and is in contact with the third guide surface 4631, the fourth guide surface 4639 and the roller surface 4716. Moreover, the third central portion 4433 is spaced apart from the surface 4661 of the pulley 4660. Thus, when axial tension is applied to the second cable 4440 for pitch movements or movement of the second tool member 4482 for yaw or grip movements, the second roller 4714 rotates along with movement of the third central portion 4433. The rotation of the second roller 4714 is based on contact with the cable 4440 at the roller surface 4716, and reduces friction that would otherwise occur when the cable slides against the surfaces of the second link 4610 when tension is applied for pitch, yaw, or grip movements. Further, the roller 4714 advantageously reduces friction at a position along the curved guide path 4625 proximate to the third guide surface 4631 where high tensile stress is applied when the cable is tightly retained within the curved guide path about the bend radius $R_3$. In some embodiments, the radius of curvature $R_3$ of the first and second guide surface 4631, 4639 is larger than the radius $R_4$ of the roller 4714. In some embodiments, the radius of curvature $R_3$ is at least twice as large as the radius $R_4$.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments, however, any of the links, tool members, tension members, or components described herein can be monolithically constructed.

Although the instruments are generally shown as having a second axis of rotation $A_2$ that is normal to the first axis of rotation $A_1$, in other embodiments, any of the instruments described herein can include a second axis of rotation $A_2$ that is offset from the first axis of rotation $A_1$ by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

For example, in some embodiments an instrument can include a tension member that is twisted as described above with reference to the instrument 4400 and that also has one or more links (e.g., a first link or a second link) that include and inner guide surface or an outer guide surface as described above with reference to the instrument 3400. Thus, in some embodiments, the instrument can include a wrist assembly that defines a guide surface that can be curved along a longitudinal center line and that can have a linear surface along a cross-section normal to the longitudinal center line.

What is claimed is:

1. An apparatus, comprising:

an instrument shaft;

a link operably coupled between the instrument shaft and a tool member;

a ball captively coupled to the link, the ball positioned to at least partially define a curved guide path within the link; and a tension member operably coupled to the tool member, the tension member including a first portion and a second portion, wherein:

the first portion is within the guide path, on a condition that the link is in a first orientation relative to the instrument shaft, the first portion of the tension member is in contact with the ball, the second portion is coupled to the tool member, and a movement of the tension member along the guide path urges the tool member to rotate relative to the link.

2. The apparatus of claim 1, wherein:

the link includes a first guide surface and a second guide surface separated by a pocket;

the ball is captively coupled within the pocket; and a surface of the ball, the first guide surface and the second guide surface are each aligned with a portion of the guide path.

3. The apparatus of claim 2, wherein:
a tangent line to the surface of the ball is tangent to the guide path that is defined by the first guide surface, the second guide surface and the ball.
4. The apparatus of claim 2, wherein:
on a condition the link is in a second orientation relative to the instrument shaft, the first portion of the tension member is spaced apart from the ball; and
the second orientation is different from the first orientation.
5. The apparatus of claim 1, wherein:
the apparatus further comprises a pulley coupled to the link;
on the condition the link is in the first orientation, the first portion of the tension member is spaced apart from the pulley; and
on the condition the link is in a second orientation relative to the instrument shaft, the first portion of the tension member is in contact with the pulley.
6. The apparatus of claim 1, wherein:
the tool member comprises a pulley portion;
the second portion of the tension member is wrapped about the pulley portion;
the tension member defines a fleet angle between a pulley coupled to the link and the pulley portion of the tool member; and
the fleet angle is less than about 10 degrees.
7. The apparatus of claim 1, wherein:
the link is rotatable relative to the instrument shaft about a first axis;
a distal end portion of the link is coupled to the tool member that is rotatable relative to the link about a second axis;
the link has a centerline; and
the guide path is offset from the centerline of the link such that movement of the tension member urges the link to rotate about the first axis.
8. An apparatus, comprising:
an instrument shaft;
a tool member including a pulley portion;
a link operably coupled between the instrument shaft and the tool member, the link including a guide surface at least partially defining a curved guide path; and
a tension member operably coupled to the tool member, the tension member including a first portion and a second portion, wherein:
the first portion is within the guide path,
the second portion is coupled to the tool member,
the tension member defines a fleet angle between the guide surface of the link and the pulley portion of the tool member,
the fleet angle is less than about 10 degrees, and
a movement of the tension member along the guide path urges the tool member to rotate relative to the link.
9. The apparatus of claim 8, wherein:
the pulley portion is coupled to a distal end portion of the link by a pin; and
the second portion of the tension member is wrapped about the pulley portion offset from the pin such that movement of the tension member urges the tool member to rotate about the pin.
10. The apparatus of claim 9, wherein:
the link is a second link;
a proximal end portion of the second link is rotatably coupled about a first axis to a first link;
the first link is fixedly coupled to the instrument shaft; and
the movement of the tension member urges the tool member to rotate about a second axis.
11. The apparatus of claim 8, wherein:
on a condition the link is in a first orientation relative to the instrument shaft, the first portion of the tension member is in contact with the guide surface; and
on a condition the link is in a second orientation relative to the instrument shaft different from the first orientation, the tension member is spaced apart from the guide surface.
12. The apparatus of claim 11, further comprising:
a pulley rotatably coupled to the link at a centerline of the link.
13. The apparatus of claim 12, wherein:
on the condition the link is in the first orientation, the first portion of the tension member is spaced apart from the pulley; and
on the condition the link is in the second orientation, the first portion of the tension member is in contact with the pulley.
14. The apparatus of claim 8, wherein:
the link includes a roller offset laterally from a centerline of the link; and
the guide surface and the roller at least partially defining the guide path offset laterally from the centerline.
15. The apparatus of claim 8, wherein:
the guide surface defines a pocket;
a roller is positioned partially within the pocket;
the roller includes a roller surface; and
a tangent line to the roller surface is tangent to the guide path.
16. The apparatus of claim 15, wherein:
the roller is a ball captively coupled within the pocket.
17. The apparatus of claim 15, wherein:
the guide path is characterized by a guide path radius of curvature that is larger than a radius of the roller.
18. The apparatus of claim 15, wherein:
the roller is a first roller, the tool member is a first tool member, and the tension member is a first tension member;
the apparatus includes a second roller rotatably coupled to the link at a position that is offset laterally from a centerline opposite the first roller;
the apparatus includes a second tension member having a third portion and a fourth portion;
on a condition the link is in a first orientation relative to the instrument shaft, the first portion of the tension member is in contact with the guide surface;
on a condition the link is in a second orientation relative to the instrument shaft different from the first orientation, the tension member is spaced apart from the guide surface;
on the condition the link is in the first orientation, the third portion of the second tension member is in contact with the second roller;
on the condition the link is in the second orientation, the second tension member is spaced apart from the second roller;
the second portion of the second tension member is coupled to a second tool member; and
a movement of the second tension member urges the second tool member to rotate relative to the link.

* * * * *